US009089364B2

(12) United States Patent
Bhadri et al.

(10) Patent No.: US 9,089,364 B2
(45) Date of Patent: Jul. 28, 2015

(54) SELF CONTAINED ILLUMINATED INFUSION CANNULA SYSTEMS AND METHODS AND DEVICES

(71) Applicant: DOHENY EYE INSTITUTE, Los Angeles, CA (US)

(72) Inventors: Prashant Bhadri, Pico Rivera, CA (US); Ralph Kerns, Laguna Niguel, CA (US); Jaw-Chyng Lormen Lue, San Gabriel, CA (US); Matthew McCormick, Forest Falls, CA (US); Mark Humayun, Glendale, CA (US)

(73) Assignee: Doheny Eye Institute, Los Angeles, CA (US)

( * ) Notice: Subject to any disclaimer, the term of this patent is extended or adjusted under 35 U.S.C. 154(b) by 0 days.

(21) Appl. No.: 14/155,113

(22) Filed: Jan. 14, 2014

(65) Prior Publication Data
US 2014/0357957 A1 Dec. 4, 2014

Related U.S. Application Data

(63) Continuation of application No. 13/106,780, filed on May 12, 2011, now abandoned.

(60) Provisional application No. 61/334,531, filed on May 13, 2010.

(51) Int. Cl.
*A61B 1/06* (2006.01)
*A61B 17/34* (2006.01)
(Continued)

(52) U.S. Cl.
CPC ........... *A61B 17/3423* (2013.01); *A61B 3/0008* (2013.01); *A61B 17/0218* (2013.01);
(Continued)

(58) Field of Classification Search
CPC ............. A61B 3/0008; A61B 17/0218; A61B 2017/0225; A61B 17/0231; A61B 17/3421; A61B 17/3423; A61F 9/00736
USPC ......... 600/105, 135, 160, 178–179, 182, 184, 600/201, 235–236, 245–246; 604/18, 21, 604/48, 93.01, 264; 606/4, 15–16, 21, 107, 606/166, 190
See application file for complete search history.

(56) References Cited

U.S. PATENT DOCUMENTS

| 3,775,606 A | 11/1973 | Bazell et al. |
| 3,798,435 A | 3/1974 | Schindl |

(Continued)

FOREIGN PATENT DOCUMENTS

| CN | 1828128 A | 9/2006 |
| EP | 1 236 439 A2 | 9/2002 |

(Continued)

OTHER PUBLICATIONS

U.S. Appl. No. 12/039,298, filed Feb. 28, 2008, Bhadri, et al., including its prosecution history, the references cited therein and the Office Actions theren.

(Continued)

*Primary Examiner* — Larry E Waggle, Jr.
(74) *Attorney, Agent, or Firm* — Knobbe Martens Olson & Bear, LLP

(57) ABSTRACT

A cannula is described having a housing, a first lumen, a second lumen, and a port capable of fluid communication with the first lumen. The second lumen configured to receive fluid from the first lumen and to direct the fluid to a surgical site. A light emitting diode light source is positionable within the housing and configured to direct light through the second lumen to the surgical site.

16 Claims, 27 Drawing Sheets

(51) Int. Cl.
  *A61B 17/02* (2006.01)
  *A61B 3/00* (2006.01)
  *A61F 9/007* (2006.01)
  *A61B 19/00* (2006.01)

(52) U.S. Cl.
  CPC ............ *A61B17/0231* (2013.01); *A61F 9/007* (2013.01); *A61F 9/00736* (2013.01); *A61B 17/3421* (2013.01); *A61B 17/3462* (2013.01); *A61B 2017/0225* (2013.01); *A61B 2019/521* (2013.01); *A61B 2019/5206* (2013.01)

(56) References Cited

U.S. PATENT DOCUMENTS

| | | | |
|---|---|---|---|
| 3,884,238 | A | 5/1975 | O'Malley et al. |
| 3,990,453 | A | 11/1976 | Douvas et al. |
| 4,019,514 | A | 4/1977 | Banko |
| 4,117,843 | A | 10/1978 | Banko |
| 4,168,707 | A | 9/1979 | Douvas et al. |
| 4,196,460 | A | 4/1980 | Schreckendgust |
| 4,200,106 | A | 4/1980 | Douvas et al. |
| 4,311,138 | A * | 1/1982 | Sugarman ............... 604/165.02 |
| 4,324,243 | A | 4/1982 | Helfgott et al. |
| 4,546,761 | A * | 10/1985 | McCullough ............... 600/184 |
| 4,551,129 | A * | 11/1985 | Coleman et al. ............... 604/21 |
| 4,651,257 | A | 3/1987 | Gehly |
| 4,820,264 | A * | 4/1989 | Matsui et al. ............... 604/21 |
| 5,009,487 | A | 4/1991 | Reiner |
| 5,115,124 | A | 5/1992 | Muto et al. |
| 5,147,354 | A | 9/1992 | Boutacoff et al. |
| 5,219,444 | A | 6/1993 | Chiaramonte et al. |
| 5,419,323 | A | 5/1995 | Kittrell et al. |
| 5,421,337 | A | 6/1995 | Richards-Kortum et al. |
| 5,422,792 | A | 6/1995 | Neumann |
| 5,425,730 | A * | 6/1995 | Luloh ............... 606/15 |
| 5,433,702 | A | 7/1995 | Zelman et al. |
| 5,554,097 | A | 9/1996 | Guy |
| 5,562,100 | A | 10/1996 | Kittrell et al. |
| 5,570,698 | A | 11/1996 | Liang et al. |
| 5,586,163 | A | 12/1996 | Goldstein |
| 5,612,540 | A | 3/1997 | Richards-Kortum et al. |
| 5,634,711 | A | 6/1997 | Kennedy et al. |
| 5,697,373 | A | 12/1997 | Richards-Kortum et al. |
| 5,699,795 | A | 12/1997 | Richards-Kortum et al. |
| 5,725,514 | A | 3/1998 | Grinblat et al. |
| 5,733,739 | A | 3/1998 | Zakim et al. |
| 5,818,052 | A | 10/1998 | Elabd |
| 5,842,995 | A | 12/1998 | Mahadevan-Jansen et al. |
| 5,918,973 | A | 7/1999 | Nojiri |
| 5,920,399 | A | 7/1999 | Sandison et al. |
| 5,957,902 | A | 9/1999 | Teves |
| 5,989,262 | A | 11/1999 | Josephberg |
| 5,993,001 | A | 11/1999 | Bursell et al. |
| 6,016,038 | A | 1/2000 | Mueller et al. |
| 6,059,792 | A | 5/2000 | Josephberg |
| 6,117,127 | A | 9/2000 | Helmreich et al. |
| 6,135,965 | A | 10/2000 | Tumer et al. |
| 6,150,774 | A | 11/2000 | Mueller et al. |
| 6,158,437 | A | 12/2000 | Vagley |
| 6,160,835 | A | 12/2000 | Kwon |
| 6,166,496 | A | 12/2000 | Lys et al. |
| 6,178,346 | B1 | 1/2001 | Amundson et al. |
| 6,183,086 | B1 | 2/2001 | Neubert |
| 6,206,014 | B1 | 3/2001 | Cameron, III et al. |
| 6,211,626 | B1 | 4/2001 | Lys et al. |
| 6,230,046 | B1 | 5/2001 | Crane et al. |
| 6,270,491 | B1 | 8/2001 | Toth et al. |
| 6,280,059 | B1 | 8/2001 | Ito et al. |
| 6,292,901 | B1 | 9/2001 | Lys et al. |
| 6,340,868 | B1 | 1/2002 | Lys et al. |
| 6,357,877 | B2 | 3/2002 | Takada |
| D457,667 | S | 5/2002 | Piepgras et al. |
| D457,669 | S | 5/2002 | Piepgras et al. |
| D457,974 | S | 5/2002 | Piepgras et al. |
| D458,395 | S | 6/2002 | Piepgras et al. |
| 6,405,863 | B1 | 6/2002 | Dhindsa |
| 6,425,677 | B1 | 7/2002 | Chuang |
| 6,436,035 | B1 | 8/2002 | Toth et al. |
| D463,610 | S | 9/2002 | Piepgras et al. |
| 6,459,919 | B1 | 10/2002 | Lys et al. |
| D468,035 | S | 12/2002 | Blanc et al. |
| 6,499,863 | B2 | 12/2002 | Dewald |
| 6,513,962 | B1 | 2/2003 | Mayshack et al. |
| 6,528,954 | B1 | 3/2003 | Lys et al. |
| 6,539,942 | B2 | 4/2003 | Schwartz et al. |
| 6,540,390 | B2 | 4/2003 | Toth et al. |
| 6,548,967 | B1 | 4/2003 | Dowling et al. |
| 6,577,080 | B2 | 6/2003 | Lys et al. |
| 6,579,255 | B2 | 6/2003 | Kadziauskas et al. |
| 6,593,101 | B2 | 7/2003 | Richards-Kortum et al. |
| 6,608,453 | B2 | 8/2003 | Morgan et al. |
| 6,623,500 | B1 | 9/2003 | Cook et al. |
| 6,624,597 | B2 | 9/2003 | Dowling et al. |
| 6,639,674 | B2 | 10/2003 | Sokolov et al. |
| 6,652,452 | B1 | 11/2003 | Seifert et al. |
| 6,685,730 | B2 | 2/2004 | West et al. |
| 6,717,376 | B2 | 4/2004 | Lys et al. |
| 6,720,745 | B2 | 4/2004 | Lys et al. |
| D491,678 | S | 6/2004 | Piepgras |
| D492,042 | S | 6/2004 | Piepgras |
| 6,766,184 | B2 | 7/2004 | Utzinger et al. |
| 6,769,546 | B2 | 8/2004 | Busch |
| 6,774,584 | B2 | 8/2004 | Lys et al. |
| 6,777,891 | B2 | 8/2004 | Lys et al. |
| 6,781,329 | B2 | 8/2004 | Mueller et al. |
| 6,786,628 | B2 | 9/2004 | Steen et al. |
| 6,788,011 | B2 | 9/2004 | Mueller et al. |
| 6,824,294 | B2 | 11/2004 | Cao |
| 6,886,964 | B2 | 5/2005 | Gardiner et al. |
| 6,934,576 | B2 | 8/2005 | Camacho et al. |
| 6,963,175 | B2 | 11/2005 | Archenhold et al. |
| 6,964,490 | B2 | 11/2005 | Scholz |
| 6,965,205 | B2 | 11/2005 | Piepgras et al. |
| 6,967,448 | B2 | 11/2005 | Morgan et al. |
| 6,975,079 | B2 | 12/2005 | Lys et al. |
| 7,014,336 | B1 | 3/2006 | Ducharme et al. |
| 7,020,370 | B2 | 3/2006 | Harris |
| 7,038,398 | B1 | 5/2006 | Lys et al. |
| 7,048,379 | B2 | 5/2006 | Miller et al. |
| 7,063,436 | B2 | 6/2006 | Steen et al. |
| 7,064,498 | B2 | 6/2006 | Dowling et al. |
| 7,116,437 | B2 | 10/2006 | Weinstein et al. |
| 7,130,115 | B2 | 10/2006 | Olszak et al. |
| 7,132,785 | B2 | 11/2006 | Ducharme |
| 7,161,311 | B2 | 1/2007 | Mueller et al. |
| 7,161,313 | B2 | 1/2007 | Piepgras et al. |
| 7,174,094 | B2 | 2/2007 | Steinkamp |
| 7,184,610 | B2 | 2/2007 | Weinstein et al. |
| 7,186,003 | B2 | 3/2007 | Dowling et al. |
| 7,229,202 | B2 | 6/2007 | Sander |
| 7,236,815 | B2 | 6/2007 | Richards-Kortum et al. |
| 7,245,273 | B2 | 7/2007 | Eberl et al. |
| 7,255,457 | B2 | 8/2007 | Ducharme et al. |
| 7,270,439 | B2 | 9/2007 | Horrell et al. |
| 7,284,861 | B2 | 10/2007 | Fuieda |
| 7,308,296 | B2 | 12/2007 | Lys et al. |
| 7,311,401 | B2 | 12/2007 | Goldfain et al. |
| 7,365,844 | B2 | 4/2008 | Richards-Kortum et al. |
| 7,387,405 | B2 | 6/2008 | Ducharme et al. |
| 7,420,153 | B2 | 9/2008 | Palmer et al. |
| 7,422,327 | B2 | 9/2008 | Smith |
| 7,458,375 | B2 | 12/2008 | Schwartz et al. |
| 7,488,088 | B2 | 2/2009 | Brukilacchio |
| 7,488,101 | B2 | 2/2009 | Brukilacchio |
| 7,499,634 | B2 | 3/2009 | Yogesan et al. |
| 7,572,028 | B2 | 8/2009 | Mueller et al. |
| 7,578,391 | B2 | 8/2009 | Nakamura |
| 7,614,763 | B2 | 11/2009 | Leibinger et al. |
| 7,625,098 | B2 | 12/2009 | Rains, Jr. et al. |
| 7,652,772 | B2 | 1/2010 | Backman et al. |
| 7,654,716 | B1 | 2/2010 | Bhadri et al. |
| 7,658,708 | B2 | 2/2010 | Schwartz et al. |
| 7,677,730 | B2 | 3/2010 | Shimizu |

(56) References Cited

U.S. PATENT DOCUMENTS

| | | | |
|---|---|---|---|
| 7,699,864 B2 | 4/2010 | Kick et al. |
| 7,710,007 B2 | 5/2010 | Liang |
| 7,731,387 B2 | 6/2010 | Cortenraad et al. |
| 7,762,664 B2 | 7/2010 | Fink |
| 7,772,534 B2 | 8/2010 | Ito |
| 7,783,346 B2 | 8/2010 | Smith et al. |
| 7,801,590 B2 | 9/2010 | Feldman et al. |
| D626,238 S | 10/2010 | Zinnanti |
| 7,845,823 B2 | 12/2010 | Mueller et al. |
| 7,850,334 B2 | 12/2010 | Holder et al. |
| 8,002,783 B2 | 8/2011 | Vercellotti et al. |
| 8,097,865 B2 | 1/2012 | Westphal et al. |
| 8,172,834 B2 | 5/2012 | Bhadri et al. |
| 8,444,629 B2 | 5/2013 | Manna et al. |
| 8,496,681 B2 | 7/2013 | Easley |
| 8,525,059 B2 | 9/2013 | Berger et al. |
| 2002/0025298 A1 | 2/2002 | Blumenkranz et al. |
| 2002/0101568 A1 | 8/2002 | Eberl et al. |
| 2003/0035301 A1 | 2/2003 | Gardiner et al. |
| 2003/0103262 A1 | 6/2003 | Descour et al. |
| 2003/0112639 A1 | 6/2003 | Stack |
| 2003/0218755 A1 | 11/2003 | Wei et al. |
| 2004/0004846 A1* | 1/2004 | Steen et al. .................. 362/555 |
| 2004/0023415 A1 | 2/2004 | Sokolov et al. |
| 2004/0032750 A1 | 2/2004 | Watts et al. |
| 2004/0064053 A1 | 4/2004 | Chang et al. |
| 2004/0090796 A1 | 5/2004 | Steen et al. |
| 2004/0181133 A1 | 9/2004 | Al-Ali |
| 2005/0047172 A1 | 3/2005 | Sander |
| 2005/0075628 A1 | 4/2005 | Cazzini et al. |
| 2005/0099824 A1* | 5/2005 | Dowling et al. .............. 362/572 |
| 2005/0128184 A1 | 6/2005 | McGreevy |
| 2005/0135095 A1 | 6/2005 | Geissler |
| 2005/0157263 A1 | 7/2005 | Sakata et al. |
| 2005/0182321 A1 | 8/2005 | Frangioni |
| 2005/0222499 A1 | 10/2005 | Banik et al. |
| 2005/0283138 A1 | 12/2005 | Tashiro et al. |
| 2006/0120250 A1 | 6/2006 | Awamura et al. |
| 2006/0134001 A1 | 6/2006 | Frangioni |
| 2006/0152172 A9 | 7/2006 | Mueller et al. |
| 2006/0228256 A1 | 10/2006 | McDevitt et al. |
| 2006/0257941 A1 | 11/2006 | McDevitt et al. |
| 2006/0257991 A1 | 11/2006 | McDevitt et al. |
| 2006/0257992 A1 | 11/2006 | McDevitt et al. |
| 2006/0257993 A1 | 11/2006 | McDevitt et al. |
| 2006/0272979 A1 | 12/2006 | Lubbers et al. |
| 2006/0282064 A1 | 12/2006 | Shimizu et al. |
| 2007/0038121 A1 | 2/2007 | Feldman et al. |
| 2007/0115658 A1 | 5/2007 | Mueller et al. |
| 2007/0173718 A1 | 7/2007 | Richards-Kortum et al. |
| 2007/0179430 A1* | 8/2007 | Smith et al. .................. 604/20 |
| 2007/0244367 A1 | 10/2007 | Caffey et al. |
| 2008/0029708 A1 | 2/2008 | Olsen et al. |
| 2008/0038738 A1 | 2/2008 | Weigum et al. |
| 2008/0051629 A1 | 2/2008 | Sugiyama et al. |
| 2008/0095714 A1 | 4/2008 | Castella et al. |
| 2008/0167644 A1 | 7/2008 | Shelton et al. |
| 2008/0200761 A1 | 8/2008 | Schwartz et al. |
| 2008/0208000 A1 | 8/2008 | Schwartz et al. |
| 2008/0208233 A1 | 8/2008 | Barnes et al. |
| 2008/0308098 A1 | 12/2008 | Schwartz et al. |
| 2009/0009759 A1 | 1/2009 | Backman et al. |
| 2009/0016075 A1 | 1/2009 | Bhadri et al. |
| 2009/0068108 A1 | 3/2009 | Sokolov et al. |
| 2009/0146583 A1 | 6/2009 | Bhadri et al. |
| 2009/0237920 A1 | 9/2009 | Dallas et al. |
| 2010/0002428 A1 | 1/2010 | Hall et al. |
| 2010/0026957 A1 | 2/2010 | Tanguay et al. |
| 2010/0093561 A1 | 4/2010 | Rantala et al. |
| 2010/0095969 A1 | 4/2010 | Schwartz et al. |
| 2010/0134303 A1 | 6/2010 | Perkins |
| 2010/0137687 A1 | 6/2010 | Schwartz et al. |
| 2010/0157620 A1 | 6/2010 | Bhadri et al. |
| 2010/0210951 A1 | 8/2010 | Rahman et al. |
| 2010/0262017 A1 | 10/2010 | Frangioni |
| 2010/0262020 A1 | 10/2010 | Backman et al. |
| 2010/0321772 A1 | 12/2010 | Reimer et al. |
| 2011/0112518 A1 | 5/2011 | Stanton |
| 2011/0282160 A1 | 11/2011 | Bhadri et al. |
| 2011/0282161 A1 | 11/2011 | Bhadri et al. |
| 2011/0295193 A1 | 12/2011 | Fitgerald et al. |
| 2012/0232540 A1 | 9/2012 | Baur et al. |
| 2013/0009606 A1 | 1/2013 | Smith et al. |

FOREIGN PATENT DOCUMENTS

| | | |
|---|---|---|
| EP | 2 441 393 B1 | 4/2012 |
| GB | 1349881 | 4/1974 |
| JP | 03-047249 | 2/1991 |
| JP | 2005528733 | 9/2005 |
| JP | 2007-044245 | 2/2007 |
| WO | WO 92/20310 | 11/1992 |
| WO | WO 98/06338 | 2/1998 |
| WO | WO 2004/105631 A1 | 12/2004 |
| WO | WO2008/106590 | 9/2008 |
| WO | WO 2008/152378 A2 | 12/2008 |
| WO | WO 2010/030850 A2 | 3/2010 |

OTHER PUBLICATIONS

Everdell, et al., "Improving Ocular Disease Screening by LED Illumination of the Eye"; Medical News Today; press release available online at http://www.medicalnewstoday.com/articles/199575.php on Sep. 1, 2010.

International Search Report and Written Opinion dated Oct. 2, 2009 for PCT Application Serial No. PCT/US09/41723.

PCT International Preliminary Report on Patentability dated Sep. 1, 2009 for PCT Application No. PCT/US08/55277 filed Feb. 28, 2008.

International Search Report and Written Opinion dated Jan. 24, 2008 for PCT Application No. PCT/US05/05521 filed Feb. 22, 2005.

International Preliminary Report on Patentability dated Feb. 24, 2009 for PCT Application No. PCT/US05/05521 filed Feb. 22, 2005.

International Preliminary Report on Patentability dated Sep. 1, 2009 for PCT Application No. PCT/US08/55277 filed Feb. 28, 2008.

International Search Report and Written Opinion dated Jul. 28, 2008 for PCT Application No. PCT/US08/55277 filed Feb. 28, 2008.

International Search Report and Written Opinion for PCT Application No. PCT/US09/41723 dated Oct. 2, 2009.

Calhoun, et al., "The Roto-Extractor in Pediatric Ophthalmology," Tr. Am. Soc., vol. LXXIII, 1975, pp. 292-305.

Douvas, Microsurgical Roto-Extractor Instrument for Vitrectomy, New Research on the Aetiology and Surgery of Retinal Detachment, Mod. Probl. Ophtal., vol. 15, pp. 253-260 (Karger, Basel 1975).

* cited by examiner

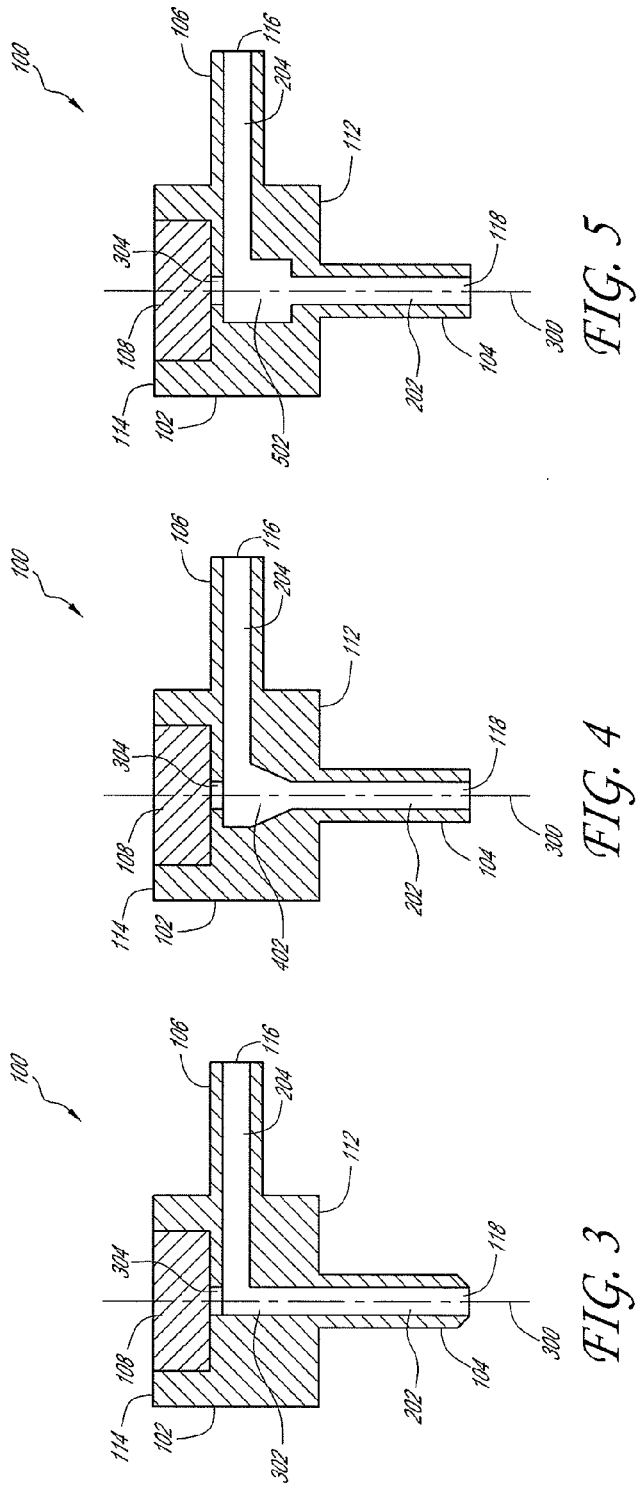

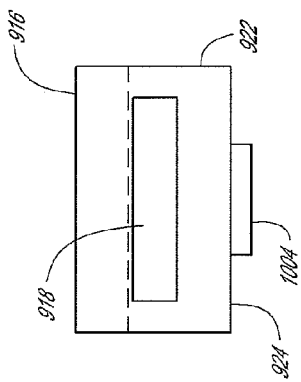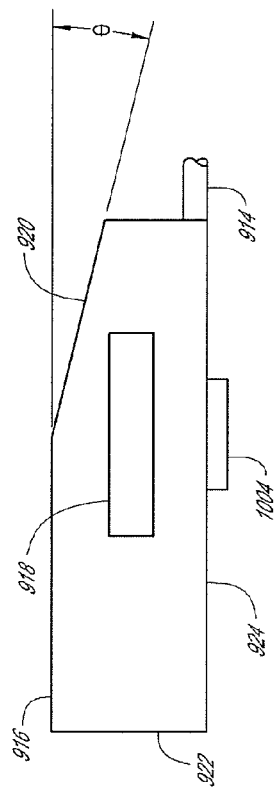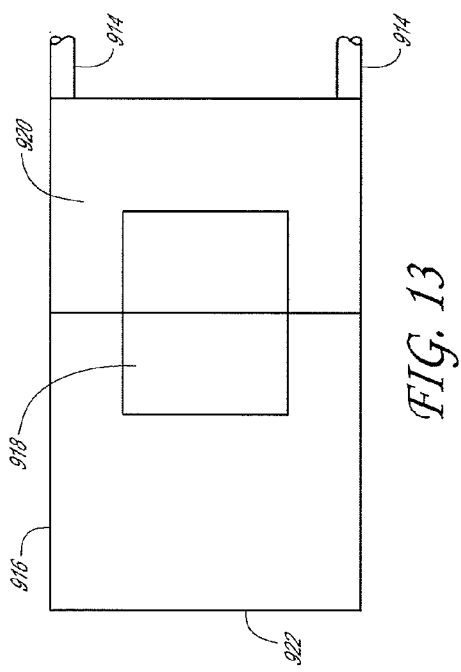

SELF CONTAINED ILLUMINATED INFUSION CANNULA SYSTEMS AND METHODS AND DEVICES

CROSS-REFERENCE TO RELATED APPLICATIONS

This application is a continuation of U.S. patent application Ser. No. 13/106,780, titled SELF CONTAINED ILLUMINATED INFUSION CANNULA SYSTEMS AND METHODS AND DEVICES, filed May 12, 2011, which claims the benefit of U.S. Provisional Patent Application No. 61/334,531, titled SELF CONTAINED ILLUMINATED INFUSION CANNULA SYSTEMS AND METHODS AND DEVICES, filed May 13, 2010. Each of the foregoing applications is hereby incorporated by reference herein in its entirety.

BACKGROUND

1. Field of the Invention

The present invention relates generally to medical surgery, and more particularly to cannula systems and methods, and more specifically, to an illuminated cannula device.

2. Description of the Related Art

Minimally invasive surgical procedures utilize assorted systems and methods, such as endoscopes or the like, for observing a surgical site or a wound to enable a surgeon to perform various surgical procedures. Generally, in some eye surgeries the surgical field is observed through the pupil. Various medical tools, devices, instruments, or the like are inserted into the vitreal cavity by performing a sclerotomy and/or other procedures to facilitate completion of the surgical procedure. The complexity of the ophthalmic surgery increases the duration of surgery and increases the number of support personnel required to assist the surgeon. Surgical procedure complexity is influenced by instrumentation introduced through various ports created by performing sclerotomies that are controlled by the surgeon. For example, generally, three ports can be created during a posterior operative surgical procedure, although additional or fewer ports can be created as necessary. The multiple ports provide various functions for the surgical procedure. For example, the multiple ports maintain the intraocular pressure through fluid infusion of a fluid, air, oil, or gas, illuminate the interior of the eye via a light source, and provide a controlled access channel for inserting surgical instruments, devices, or the like.

SUMMARY

The systems and methods disclosed herein are related to an illuminated infusion cannula for internally illuminating biological tissue, organs, body lumens, and/or body cavities to enable a surgeon to perform various orthopedic surgeries, neurosurgeries, and/or other surgical procedure. Various embodiments of the present disclosure can also relate generally to an illuminated cannula device for internally illuminating an eye to enable a surgeon to perform various surgical procedures in, on, around, and/or near the eye.

In accordance with one embodiment, the present disclosure provides a medical treatment system having a self-contained illuminated infusion cannula system, including a light source, such as a light emitting diode or an organic light emitting diode light source, located in the cannula device, and transmitting light and infusion fluid through the same cannula into the surgical site within the eyeball.

A cannula system can include a body, a light source contained within the body, an infusion port and a cannula. The infusion port can be formed in the body for receiving fluids to be delivered to a surgical site. The cannula can also be formed with the body. The cannula can have a lumen for delivering the fluids received through the infusion port and for transmitting light from the light source. In some embodiments, the system can include one or more lens or other optical elements. Some embodiments may also or alternatively include a trocar sized to pass through the cannula.

Another embodiment of a cannula system can comprise a housing element having a lumen and a port configured to provide a flow of fluid to the lumen and a light emitting diode light source. The light source can be positionable within the housing element and configured to direct light through the lumen when disposed within the housing element. The lumen can be transparent and configured to permit light to pass through the lumen from the light emitting diode light source to a surgical site. The lumen can also be configured to direct fluid to the surgical site.

A cannula system can have a body, an insert and an elongate member. The body can have a proximal portion and a distal portion, a first lumen extending between the proximal portion and the distal portion, and a port coupled to a second lumen. The second lumen can communicate with the first lumen. The body can also have a first aperture extending to the first lumen at the proximal portion. The insert element can have a light source positionable within the first aperture to permit light from the light source to pass through the first lumen. The elongate member can be transparent and can have a first portion and a second portion with a third lumen extending through the elongate member from the first portion to the second portion. The first portion of the elongate member can be coupled to the distal portion of the first lumen. The transparent member third lumen can permit light to pass from the light source to a surgical site and be capable of fluid communication with the port, the first lumen, and the second lumen.

In accordance with another embodiment the present disclosure provides a cannula comprising a housing element having a distal portion and a proximal portion, a first lumen extending between the proximal portion and the distal portion, and a port capable of fluid communication with the first lumen. A light emitting diode light source can be removably positionable within the housing element. The light emitting diode light source is configured to direct light through the first lumen when disposed within the housing. The light emitting diode light source comprises at least a red light emitting diode, a blue light emitting diode, and a yellow light emitting diode. The embodiment further includes a transparent second lumen having a first portion and a second portion. The first portion is coupled to the distal portion of the first lumen, and the transparent second lumen is configured to permit light to pass through from the light emitting diode light source to a surgical site. The embodiment additionally includes the transparent second lumen being configured to receive fluid from the first lumen. The diameter of the transparent second lumen is 20 gauge or smaller.

In accordance with another embodiment the present disclosure provides a cannula comprising a housing element having a distal portion and a proximal portion, a first lumen extending between the proximal portion and the distal portion, and a port capable of fluid communication with the first lumen. A light emitting diode light source can be removably positionable within the housing element. The light emitting diode light source is configured to direct light through the first lumen when disposed within the housing. The light emitting diode light source comprises at least a red light emitting diode, a blue light emitting diode, and a yellow light emitting diode. The embodiment further includes a transparent second lumen having a first portion and a second portion. The first portion is coupled to the distal portion of the first lumen, and the transparent second lumen is configured to permit light to pass through from the light emitting diode light source to a surgical site. The embodiment additionally includes the transparent second lumen being configured to receive fluid from the first lumen.

In accordance with another embodiment the present disclosure provides a cannula system comprising a body having a distal portion and a proximal portion, with a first lumen extending between the proximal portion and the distal portion and a periphery surface extending between the proximal portion and the distal portion. The embodiment further includes a port coupled to a second lumen. The second lumen communicating with the first lumen, and a first aperture extending to the first lumen. The embodiment can additionally include an insert element comprising a light emitting diode light source positionable within the first aperture to permit light from the light emitting diode light source to pass through the first lumen. The embodiment still further includes an elongate transparent member, having a first portion and a second portion, wherein a third lumen can extend through the elongate member from the first portion to the second portion, and the first portion is coupled to the distal portion of the first lumen. The transparent member third lumen can be configured to permit light to pass from the light emitting diode light source to a surgical site, and the transparent member third lumen can be capable of fluid communication with the port and the first lumen and the second lumen.

In accordance with another embodiment, the present disclosure provides a method of treating an eye. The method includes providing a cannula comprising a body having a first lumen therein, and an elongate member extending from a distal portion of the body, the elongate member having a second lumen substantially coaxial with the first lumen, the first and second lumen capable of fluid communication with a fluid source, and an insert having a light emitting diode light source, the insert positionable through a first aperture to permit light to pass through the first lumen and the second lumen. The embodiment further includes projecting an incision instrument through the first and second lumen with the insert removed to allow passage of the instrument. The embodiment additionally includes creating an incision in the eye tissue by penetrating the tissue with a sharp distal end of the incision instrument. The embodiment still further includes inserting the elongate member through the incision to position a distal portion of the elongate member such that the distal portion lies within the eye with the distal surface of the body adjacent the outer surface of the eye. The embodiment additionally includes removing the incision instrument from the transparent elongate member and the body, and positioning the insert adjacent the first lumen to permit light to pass from the light emitting diode through at least a portion of the second lumen. The embodiment still further includes illuminating the internal portion of the eye by permitting light to pass through the transparent elongate member and dispersing the light within the eye, and irrigating the interior of the eye with fluid delivered through the transparent elongate member, the fluid exiting from at least a portion of the transparent elongate member.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The foregoing and other features, aspects and advantages of the invention are described in detail below with reference to the drawings of various embodiments, which are intended to illustrate and not to limit the invention. The drawings comprise the following figures in which:

FIG. 3 is a cross-section view of the self-contained illuminated infusion cannula system of FIG. 1.

FIG. 4 is a side view of an embodiment of a self-contained illuminated infusion cannula system.

FIG. 5 is a side view of an embodiment of a self-contained illuminated infusion cannula system.

FIG. 11 is a side view of an insert portion of the self-contained illuminated infusion cannula system of FIG. 9.

FIG. 12 is a front view of an insert portion of the self-contained illuminated infusion cannula system of FIG. 9.

FIG. 13 is a top view of an insert portion of the self-contained illuminated infusion cannula system of FIG. 9.

DETAILED DESCRIPTION OF PREFERRED EMBODIMENTS

The efficiency and comfort of the surgeon during a surgical procedure can be increased with a reduction in the quantity and/or mass of the various instruments controlled by the surgeon. Thus, it is desired to reduce the number of instruments inserted into the eye during ophthalmic surgery. Challenges of known infusion and/or fiber-optic light cannulas include obtaining sufficient illumination of the inside of the eyeball at the surgical site, the need for support personnel to assist the surgeon in handling the numerous instruments, and the fatigue incurred by the surgeon while handling the appurtenant illumination and infusion instrumentation connected to the surgical control panel. Additional issues arise with the heat emitted from the light source of fiber-optic systems, the short operating life of the light sources, and the fragility of the fiber optics of such systems.

Accordingly, there is a need in the art for an improved illumination infusion cannula device or system that solves some of the disadvantages discussed above. Particularly, there is a need for a self-contained illuminated infusion cannula system that reduces the efforts and attention a surgeon needs to direct to the illumination of the surgical site during a surgical procedure, and increases the transmittance of light to the surgical site within the eyeball. Further, a need exists for an improved illumination device that provides greater durability and reliability than currently available fiber-optic light sources.

The associated drawings and specification discuss aspects and features of the disclosure in the context of several different embodiments of illuminated infusion cannula devices and methods that are configured for use in surgical procedures, in particular ophthalmic surgery. Discussing these features in connection with ophthalmic surgery provides for clarity and consistency in presenting these inventive features and concepts. However, it is to be understood that the features and concepts discussed herein can be applied to surgical methods other than ophthalmic procedures.

Figure 1:
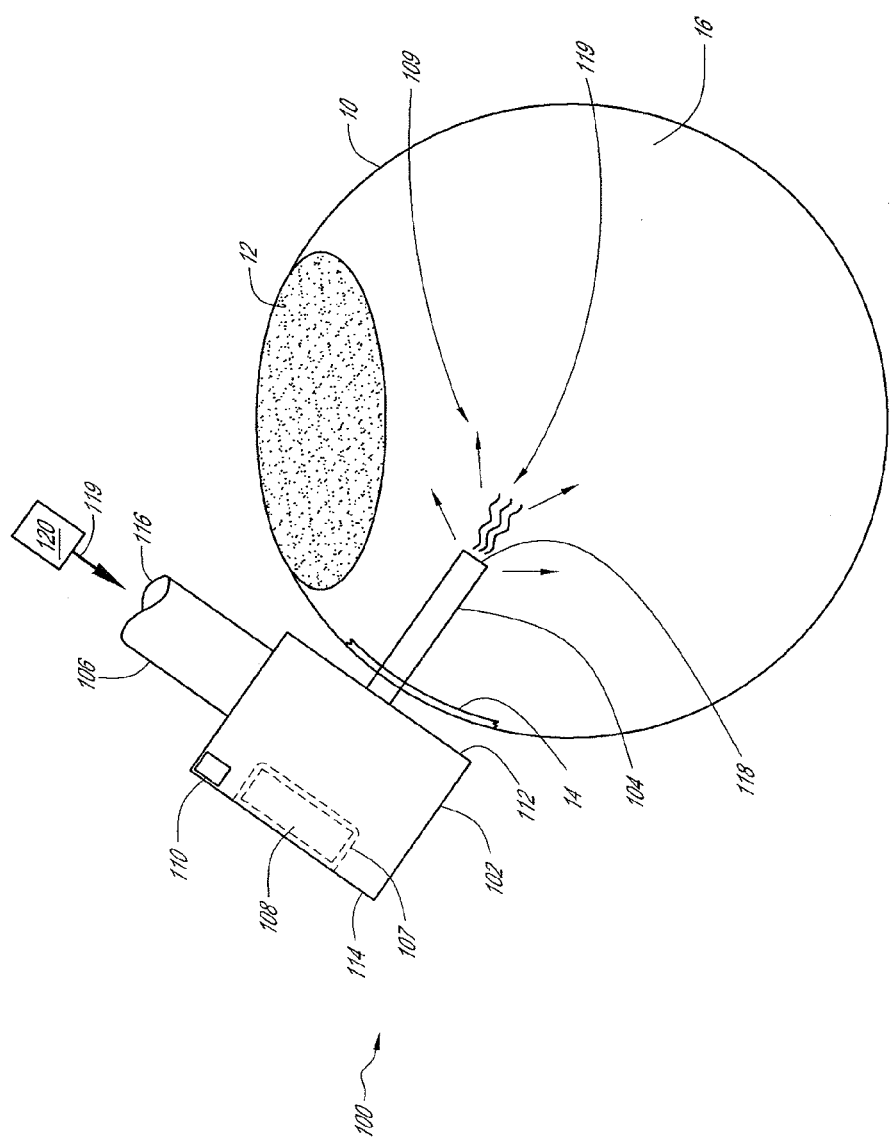
FIG. 1 is a side view of a self-contained illuminated infusion cannula system, in accordance with an embodiment inserted into the eyeball.
Figure 2:
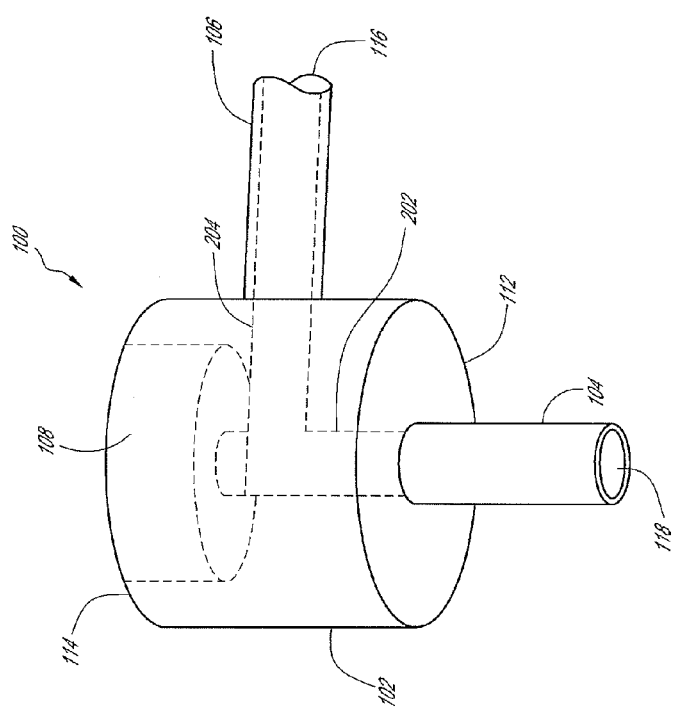
FIG. 2 is a perspective view of the self-contained illuminated infusion cannula system of FIG. 1.

With reference to FIG. 1, a side view of a self-contained illuminated infusion cannula system 100 inserted through the sclera 14 of the eyeball 10, adjacent or near the pupil 12, is shown. The cannula system 100 may operate to provide a wide-angle field of illumination to allow a surgeon to view as large of a portion of the retina and other eye features. In particular, the system 100 can allow the surgeon to visualize the anatomical structures at the posterior portion of the eye, such as other features of the fundus, e.g. blood vessels, the optic nerve, the choroid, and the like.

The self-contained illuminated infusion cannula system 100 can generally include a body 102, an elongate member or cannula 104, a conduit 106, and a light source 108. The cannula system 100 can further include a power source 110, an infusion port 116, and an outlet 118. The body or housing 102, can receive infusion fluid 119 through the infusion port 116 at a distal end of the conduit 106 and light transmittance 109 from the light source 108. The body 102 can direct fluid and permit the light to pass out the outlet 118 of the cannula 104.

The light source 108 can generate light and can be in the form of, for example, one or more of a light emitting diode (LED), an organic light emitting diode (OLED), a light bulb, or a lamp. The light source 108 contained in the infusion cannula system 100 provides certain benefits over currently available fiber optic systems, such as not being tethered to a separate light source to generate the light directed down the fiber optic. Thus, the light source 108 allows for a self-contained system where the light source 108 can be contained within the body 102 of the system 100.

The infusion port 116 can be coupled to a fluid source 120 to provide a fluid inlet flow of infusion fluid. The fluid source 120 can be part of, for example, a remote console, or control, system that is not shown. The conduit 106 can extend from the infusion port 116 at one end to the body 102 at the other end. The cannula 104 can extend from a distal end 112 of the body 102 to the outlet 118 at a distal end of the cannula 104. The cannula outlet 118 can establish the furthest point, or location, of entry within the tissue, or eyeball as shown in FIG. 1, at a surgical site 16.

With reference to FIGS. 1-5, the illuminated infusion cannula system 100 can function to provide a combination of infusion fluid 119 and light 109 to the surgical site 16 during ophthalmic surgery. The infusion fluid 119 can be provided by a remote fluid source 120 that can deliver the fluid inlet flow via a flexible tube, not shown, for example, to the infusion port 116. The flexible tube can generally be biologically compatible to prevent detrimental contamination of the eye and associated tissue, e.g., silicone or the like. In an embodiment, the infusion fluid 119 can be a saline fluid to maintain the intraocular pressure and irrigate the surgical site. In an embodiment, the infusion fluid 119 can be a treatment fluid to treat the eye, or an anatomical feature of the surgical site, or an adjacent region of the anatomy.

With continued reference to FIGS. 1-5, the infusion port 116 can be coupled to the conduit 106, which in turn is coupled to the body 102. The body 102 can include a distal end or surface 112 that can be placed adjacent the outer surface of the eye 10. The distal end 112 can provide a support surface for the cannula system such that the cannula can be self-supported, avoiding the need for continuous handling by a surgeon or other surgical personnel for the duration of the surgical procedure. The distal end 112 can generally rest adjacent and/or on the sclera, or the outer surface of the eye, such that the LED 108 light source is between about 0.015 inches and about 0.050 inches from the outer surface of the sclera, more preferably between about 0.020 inches and about 0.040 inches. The body can further include a proximal end or surface 114 which generally opposes the distal end 112 and, in an embodiment, can generally define the outermost proximal surface of the contiguous cannula system.

In the illustrated embodiments of FIGS. 1-5, the body 102 can include several internal geometric features or characteristics that facilitate the transmittal of light 109 and the delivery of the infusion fluid 119 to the eye 10. The body 102 can include flow passages or lumens, for example, a first lumen 202, a second lumen 204, a chamber 302, and a centerline axis 300 (FIG. 3). The body 102 can further include light source related features, for example, an LED cavity 107 and a lens 304 (FIG. 3-5).

Internal to the body 102, the first lumen 202 can define a generally circular cross-sectional passageway extending from the proximal most portion of the cannula system 100 to the distal most portion of the cannula system 100. Thus, the first lumen 202 can extend through the body 102 and the cannula 104. The first lumen 202 can generally be concentric with the centerline axis 300. The infusion fluid 119 provided via the second lumen 204, flows through the first lumen 202; hence the first lumen 202 is a common lumen for delivering infusion fluid 119 and transmitting light 109 of the LED 108 through the cannula 104. In an embodiment, the first lumen 202 can include a cross-sectional passageway that can be any geometric shape, for example, polygonal, oval, triangular, rectangular, or the like.

The first lumen 202 can provide an additional capability, which is that of an accessway for an incision instrument, not shown, from the proximal surface 114 to the outlet 118 of the cannula 104. The incision instrument or trocar can include a sharp distal tip that can facilitate cutting or puncturing the sclera 14 of the eye 10. The cannula 104 can pass through this incision into the vitreous cavity of the eye 10. The first lumen 202 can allow the trocar to be inserted through the cannula system 100, create the incision, and be removed from the cannula system 100 upon insertion of the cannula 104 into the eye 10. As described below in detail, the insertion of an independent trocar through the first lumen 202 may require access through the LED cavity 107. Thus, the LED 108 and any optical elements can be removed, or moved aside, prior to trocar insertion, then installed or inserted into the cannula system 100 after the cannula 104 is inserted into the eye 10.

The second lumen 204 can define a generally circular cross-sectional passageway extending from the infusion port 116, through the conduit 106, and meeting the first lumen 202 at a junction adjacent the centerline axis 300. The second lumen 204 can provide the passageway to deliver the infusion fluid 119 from the fluid source 120 into the first lumen 202, whereupon the fluid can provide a light transmittance medium for the light 109 emitted by the LED 108. The second lumen 204 and the conduit 106 can be sized to receive, or couple to, the fluid source tubing, not shown.

The fluid source tubing can generally have an internal diameter of between about 0.030 inches and about 0.125 inches, more preferably between about 0.050 inches and about 0.070 inches. Accordingly, the infusion port 116 can be sized to receive the tubing within the infusion port 116 internal diameter, or more preferably, to be received within the tubing internal diameter, thus having the tubing fit over the infusion port outer diameter. The second lumen 204 cross-section can generally have a diameter of between about 0.030 inches and about 0.125 inches, more preferably between about 0.050 inches and about 0.070 inches, as well. In an embodiment, the first lumen 202 can include a cross-sectional passageway that can be any geometric shape, for example, polygonal, oval, triangular, rectangular, or the like.

With reference to FIGS. 2-5, cross-section views of several embodiments of the cannula system 100 with various embodiments of a chamber located internal to the body 102 are shown. The body 102 can have the chamber 302 that can define the hollow volume where the first lumen 202 joins the second lumen 204. The chamber 302 can define the region where the flow of infusion fluid 119 changes direction from that of the second lumen 204 to the direction of the first lumen 202. Thus, the chamber 302 is a selective portion of the first lumen 202, and to a lesser degree, of the second lumen 204.

In the illustrated embodiment of FIG. 3, the infusion fluid 119 flows through an approximately 90 degree bend, or elbow, in the lumens of the body 102. Other degrees of bend are possible. The chamber 302 can generally define the region of highest flow disturbances in the infusion fluid 119 as the infusion fluid 119 is delivered from the flow source tubing to the flow outlet 118 of cannula 104. The flow disturbances within the chamber 302 resulting from the change in flow direction generally results in a negligible effect on the transmittance of light 109 being emitted from the LED 108 downstream into the eye 10. In some embodiments, the space between the fluid pathway and light emitting diode can be optimized so that the cross-sectional area of the fluid conduit remains substantially constant in order to maximize and/or substantially maximize high light transmittance and/or high fluid flow rate.

With reference now to FIG. 4, a further embodiment of an internal chamber 402 of the body 102 is shown. As described above, the chamber can define the region where the lumens 202, 204 join and the infusion fluid 119 makes any required change in direction. The chamber 402, as shown in FIG. 4, can provide a converging diameter for the infusion fluid 119 and light 109 after the change in direction from the lumen 204 into the lumen 202. The diameter of the chamber 402 can be greater than the diameter, or width, of the lens 304, or the dispersion angle of the LED 108 in the absence of a lens installed in the body 102. The greater diameter of the chamber 402 can thus distance the LED's emitted or directed light 109 from the flow disturbances due to internal surface discontinuities and directional changes represented by the corners, or changes in surface direction, of the chamber 402. In an embodiment, the change in direction of the light can be further influenced by features to improve the refractive index differences in the chamber and assist the light 109 passing through the first lumen 202, e.g. coatings, material selection, or the like. The increased distance can reduce the effect fluid flow disturbances can impart on the light 109 transmitted downstream through the first lumen 202.

With reference to FIG. 5, a further embodiment of an internal chamber 502 of the body 102 is shown. As described above, the chamber can define the region where the lumens 202, 204 join and the infusion fluid 119 makes any required change in direction. The chamber 502, as shown in FIG. 5, can provide an increased volume for the flow disturbances imparted by the change in direction of the infusion fluid 119 flow to dampen out of the flow stream, as well as distancing the flow internal surface discontinuities from the transmitted light 109. The increased distance and volume can reduce the effect fluid flow disturbances can impart on the light 109 transmitted downstream through the first lumen 202.

With reference to FIGS. 1-5, the body 102 can include the LED cavity 107, or aperture, extending from the proximal surface 114 into the body 102. The cavity 107 can removably receive the LED 108, and is sized to provide a fluid seal to prevent leaking of the infusion fluid 119 during use and operation of the cannula system 100. The sealing function can be provided by any acceptable means, for example, a tightly toleranced dimensional fit between the cavity 107 and the LED 108, a biologically compatible sealing material between the cavity 107 and the LED 108, e.g. a seal, a gasket, a viscous lubricant, or the like, or other suitable means. The LED 108 can be snapped, friction fit, or otherwise tightly located in place in the cavity 107 to prevent fluid 119 leakage. The LED 108 can generally be located concentrically to the body 102 about a centerline axis 300, as shown in FIG. 3. In an embodiment, the LED can be offset from the centerline axis 300, as described in detail below and shown in FIG. 21A. The LED 108 can be positioned to project, or transmit, light 109 internally to the body 102 through the first lumen 202, as further shown in FIGS. 2-5.

The body 102 can further include a lens 304 located along centerline axis 300 and adjacent the LED cavity 107 such that the lens can be adjacent the LED 108 and the light 109 emitted from the LED 108. The lens 304 can be integrally molded into the body 102 during fabrication. In some embodiments, the lens 304 can be fabricated independently of the body 102 and assembled into the body 102. In some embodiments, the lens 304 can be fabricated as a part of an LED housing assembly and inserted, or installed, into the body 102 upon installation of the LED housing assembly.

The lens 304, as shown in FIGS. 3-5, can converge and/or collimate the light 109 emitted from the LED 108 downstream through the first lumen 202 toward and into the eye 10 and/or filter out unwanted and/or unnecessary light wavelengths from the emitted light 109 to selectively illuminate anatomical features within and/or adjacent the eye 10. The lens 304 can further provide a sealing function within the first lumen 202 through which the incision instrument, or trocar, passes to facilitate insertion of the cannula system 100 into the eye 10. The lens 304 sealing function can be provided by any acceptable means, for example, a tightly toleranced dimensional fit between the lens 304 and the first lumen 202, a biologically compatible sealing material between the lens and the lumen 202, e.g. a seal, a gasket, a viscous lubricant, or the like, or other suitable means.

The body can be fabricated integrally with the conduit 106 and the cannula 104 to define a single piece cannula system 100. The body 102, and the cannula system 100 can be fabricated by injection molding to obtain the complex geometry and small form factor required for ophthalmic surgery and insertion into the eye 10. In some embodiments, the cannula system can be fabricated with more than one piece and can be assembled to make the cannula system 100. In some embodiments, any manufacturing method, e.g. machining, adhesive bonding, or the like, can be implemented to fabricate the cannula 104 and/or the cannula system 100.

The body 102, as shown in FIGS. 1-5, can be made of a transparent or amber material having a high percentage of light transmission to facilitate a single piece fabrication method and provide a cannula that is transparent, capable of readily dispersing the light 109 in a wide-angle distribution pattern into the vitreous cavity of the eye 10. For example, the body 102 can be made of any suitable biologically compatible material such as polyamide, polycarbonate, acrylic, silicone, or the like, or a combination thereof. In some embodiments, the cannula system 100 can include multiple individually fabricated elements, for example the cannula 104, and/or the body 102, and/or the conduit 106, that are subsequently assembled to define the cannula system 100. The individually fabricated elements can, for example, be adhesive bonded together to define the cannula system 100. In some embodiments, the body can be fabricated of an opaque material and the cannula 104 can be fabricated from a transparent material.

The body 102 can generally have a round, or circular, periphery extending between the distal end 112 and the proximal end 114. The diameter of the periphery can be between about 0.030 inches and about 0.125 inches, more preferably between about 0.050 inches and about 0.070 inches. The body 102 can have a wall thickness between about 0.010 inches to 0.030 inches. The height, or length, along the centerline axis 300 of the body 102 can generally be between about 0.030 inches and about 0.125 inches, more preferably between about 0.050 inches and about 0.070 inches.

The cannula 104, as shown in FIGS. 1-5, can be coupled to the body 102 distal end 112. The cannula 104 can be a hollow elongate member, or cylinder, providing a lumen to concurrently deliver the infusion fluid 119 and transmit light 109 emitted by the LED 108 from the body 102 into the vitreous cavity of the eye 10. The cannula 104, similar to the body 102, can be a transparent, or semi-transparent, or amber material having a high percentage of light transmission, cylinder to facilitate dispersion of the light 109 into the surgical site within the vitreous cavity along the full length of the cannula 104 sidewalls. The dispersion of the light 109, and thus the field of view at the surgical site, can be selectively controlled by geometry, transparency, and materials included in fabricating the cannula 104. As described in detail below and shown in FIG. 14, optical elements such as prisms, or the like, can be fabricated into the cannula 104. The optical elements can be fabricated and/or oriented to disperse at predetermined angles, and spaced longitudinally along the centerline axis 300 to obtain predetermined coverage for the field of view 1602, shown, for example, in FIG. 15.

The cannula 104 can generally include a small form factor to facilitate insertion, function, and interoperability with the possible assortment of additional instruments required at or adjacent the surgical site. The cannula 104 can have a relatively much smaller cross-section normal to the centerline axis 300, as compared to the body 102. The cannula 104 can include a size of between about 35 gauge and about 15 gauge, more preferably between about 30 gauge and about 20 gauge, even more preferably a size of 25 gauge or 23 gauge or 20 gauge cannula. The cannula 104 can be longitudinally sized to have a length sufficient to penetrate and extend beyond the sclera 14 of the eyeball 10 and into the vitreous cavity, yet minimize the interference with surgical site requiring visual line of sight to the surgeon and physical access to the other various instruments to perform the ophthalmic surgery. The cannula 104 can have a length of between about 2.0 mm and about 10.0 mm, more preferably between about 2.0 mm and about 3.0 mm, and still more preferably between about 2.3 mm and about 2.7 mm. The cannula 104 can protrude beyond the sclera a length of between about 01.0 mm and about 10.0 mm, more preferably between about 01.0 mm and about 3.0 mm, and still more preferably between about 1.5 mm and about 2.5 mm.

With continued reference to FIGS. 1-5, the cannula 104, as described above, can provide an accessway lumen for an incision instrument, such as a trocar, for creating an incision in the sclera 14 to facilitate insertion of the cannula 104 into the eyeball 10 and the vitreous cavity. The cannula 104 can be inserted transconjunctivally to provide for an incision that can seal suturelessly upon removal of the cannula. The elastic nature of the sclera forms a tight, or substantially tight, seal around the cannula to prevent vitreous fluid and/or infusion fluid or the like from leaking out of the incision. In an embodiment, the distal end of the cannula 104, adjacent the outlet 118, can be formed at a non-orthogonal angle, or tapered, to the centerline axis 300 and can be provided with a tapering, or sharpened, wall thickness. The sharpened and angled end can define an incision instrument capability for the cannula 104, negating the need for a separate incision instrument to extend longitudinally through the body 102 and the cannula 104 of the cannula system 100. Geometry, optical elements, optical coatings, and the like, can be implemented into the cannula 104, such as adjacent the outlet 118, to facilitate a symmetric and sufficient dispersion of the light 109 transmitted through the cannula system 100. The additional optical considerations can offset the uneven dispersion of the light 109 out of an angled end of the cannula 104.

With continued reference to FIGS. 1-5, the cannula 104, similar to the body 102, can be made from any of a variety of transparent capable materials. For example, the cannula 104 can be made of any suitable biologically compatible transparent materials such as polyamide, polycarbonate, acrylic, silicone, or the like, or a combination thereof. As described above, the cannula 104 can be integrally fabricated with the body 102 and the conduit 106 to form a single piece, or monolithic, cannula system 100. The cannula 104, and the cannula system 100 can be fabricated by injection molding to obtain the complex geometry and small form factor. A single piece, or monolithic, cannula system 100 structure can be less susceptible to breakage, providing for a more durable and/or rigid instrument. In some embodiments, the cannula system can be fabricated with more than one piece and can be assembled to make the cannula system 100. In some embodiments, any manufacturing method, e.g. machining, adhesive bonding, or the like, can be implemented to fabricate the cannula 104 and/or the cannula system 100.

The cannula system 100 can further include a conduit 106, illustrated in FIGS. 1-5. The conduit 106 can provide an accessway for the infusion fluid 119 to flow from the infusion port and fluid source tubing, to the first lumen 202 and, ultimately, the eye 10. The conduit 106 defines the portion of the second lumen 204 that is not located internally to the body 102. Therefore, the dimensional characteristics are described above with respect to the infusion port and the second lumen 204. The length of the conduit can vary according to the particular application of the cannula system 100.

With continued reference to FIGS. 1-5, the cannula system 100 can include the LED 108 that can be coupled to the body 102 within the LED cavity 107. The LED 108 advantageously provides an efficient high intensity light source requiring low power consumption with decreased light 109 transmission loss in transmitting light 109 from the LED 108 to the surgical site within the vitreous cavity of the eye 10. Additionally, the LED 108 provides a reliable, low cost light source to the cannula system 100, such that the cannula system 100 can be a disposable surgical instrument. In an embodiment, the light source can be an organic light emitting diode (OLED).

LED light sources used in/for embodiments of the present disclosure can provide various advantages. As they are based on electronic component design, LEDs are largely, if not entirely, immune from or resistant to system vibrations. LEDs can be protected from dirt and moisture, facilitating useful lifetimes that can increase to, or approach, thousands of hours, which is much higher than a non-LED light source. Further, LED-based light sources can operate at lower temperatures, and therefore have lower heat dissipation requirement, thereby eliminating complex heat sink systems commonly used for lighting techniques. Cost of a single LED system is exponentially less expensive than a standard light source system because of the simpler packaging. Additionally, LEDs are available in multiple colors/including high output efficiency.

As is known, LEDs are devices that convert electrical energy into optical energy. An LED is a semiconductor based diode, or device, including a p-doped region and a n-doped region. The principle behind an LED provides that as an electron in the conduction band recombines with a hole in the valence band, the electron makes a transition to a lower-lying energy state. This leads to the release of energy in an amount equal to the band-gap energy. In general, the energy is dissipated by phonons, i.e. heat, or photons, i.e. light. In an LED, this energy is directed into emitted light energy.

When an LED is stimulated electrically by a pulsed current or by a current produced in response to an applied voltage, electrons and hole carriers in the p-n junction recombine, emitting photons as an incoherent narrow spectrum of light. This phenomenon is termed electroluminescence, where the color, e.g. UV, Visible, or IR, of light depends on the type of the semiconductor materials used for the p-doped region and n-doped region. The optical power the LED emits can be dependent on the doping and/or the forward current through the diode interface. The frequency response of LED's are approximately 120 Hz and the light can be collimated with a lens system. Further details are provided in application Ser. No. 12/237,110 filed Sep. 24, 2008, the entirety of which is hereby incorporated by reference herein.

With continued reference to FIGS. 1-5, the LED 108 can be assembled, or potted, into a tray, or housing, that can readily assemble into the cannula system 100, in particular the LED cavity 107. The housing, similar to the body 102, cannula 104, and conduit 106, can be fabricated from any suitable biologically compatible transparent material, e.g. polyamide, polycarbonate, acrylic, silicone, or the like, or a combination thereof. In an embodiment, the housing material can be opaque except for the window area located adjacent the LED 108 light exit. The LED 108 can be encapsulated, or housed, in a transparent or semi-transparent housing and can be inserted or installed into various cannula and/or body 102 configurations configured to receive the housing, or tray, in any variety of orientations of the LED or cannula and/or positions within the cannula, either alone or in combination with filters, lenses, or any combination or quantity of each thereof.

The LED 108 parameters can provide intensity to the eye 10 of between about 4 lumens and about 25 lumens, more preferably between about 7 lumens and about 20 lumens. The wavelength of light transmitted to the eye 10, after being emitted from the LED and subsequently transmitted and conditioned through a window, filter, lens, or combination thereof, can be between about 400 nm and about 700 nm, more preferably between about 430 nm and about 660 nm. The beam size can be between about 0.2 mm and about 3.0 mm, more preferably between about 0.3 mm and about 1.4 mm, and more preferably between about 0.4 mm and about 1.0 mm. In an embodiment, the beam size is defined adjacent an optical element, such as lens 304, or the like.

The direct transmission of the LED 108 light source into the vitreous cavity of the eye 10 via the first lumen 202 and the transparent cannula 104 can advantageously minimize light transmission loss and can improve light intensity because of the adjacent positioning of the light source to the eye as compared to currently available fiber optic light systems. The use of a direct transmission LED eliminating a fiber optic line can also reduce the torque applied to the cannula system 100 by the appurtenant instruments, and can enable hands-free surgical illumination. In an embodiment, the self contained illuminated infusion cannula system 100 can reduce the number of incisions required, thereby allowing bimanual, or two ports, surgery. In an embodiment, the cannula system 100 can illuminate the eye with various colors and/or tints with and without combinational instruments. In some embodiments a fiber optic light source can be provided to augment the LED 108. In some embodiments, both a fiber optic light source and an LED may increase torque on the cannula system 100 which can be acceptable under certain conditions.

In an embodiment, the LED housing can be utilized to house an ultrasonic transducer, rather than an LED light source. The ultrasonic transducer can be implemented for treatment of the eye 10. For example, the transducer can be a high intensity focused ultrasound (HIFU) that can direct concentrated heat and/or vibration at tissue within the eye, or the transducer can be a high power focused ultrasound (HPFU) to transmit vibration across a larger area to emulsify tissue within the eye. The use of an ultrasonic transducer can be combined with any of the cannula system embodiments disclosed herein.

The power source 110 can comprise a separate power supply box from which electrical lines can be coupled to the LED 108 light source (FIG. 1). The electrical lines can be thin, lightweight insulated wires that can apply minimal and/or substantially minimal torque on a cannula system 100 inserted and resting on, or adjacent, the sclera 14 of the eye 10. The power source 110 energy supply component can be an AC source or a DC source (for example, a battery or rectified AC source) and can also power an electronic control panel system, not shown. The electronic system, in turn, can consist of the microprocessor circuitry, described in detail below, which can be operational to provide a signal, for example a current pulse, to the one or more LED 108 light sources. In addition, the circuitry can include a converter/regulator, or a boost converter. For battery-powered embodiments, a converter can be operable to step up the battery voltage to that required for LED light sources.

Figure 6:
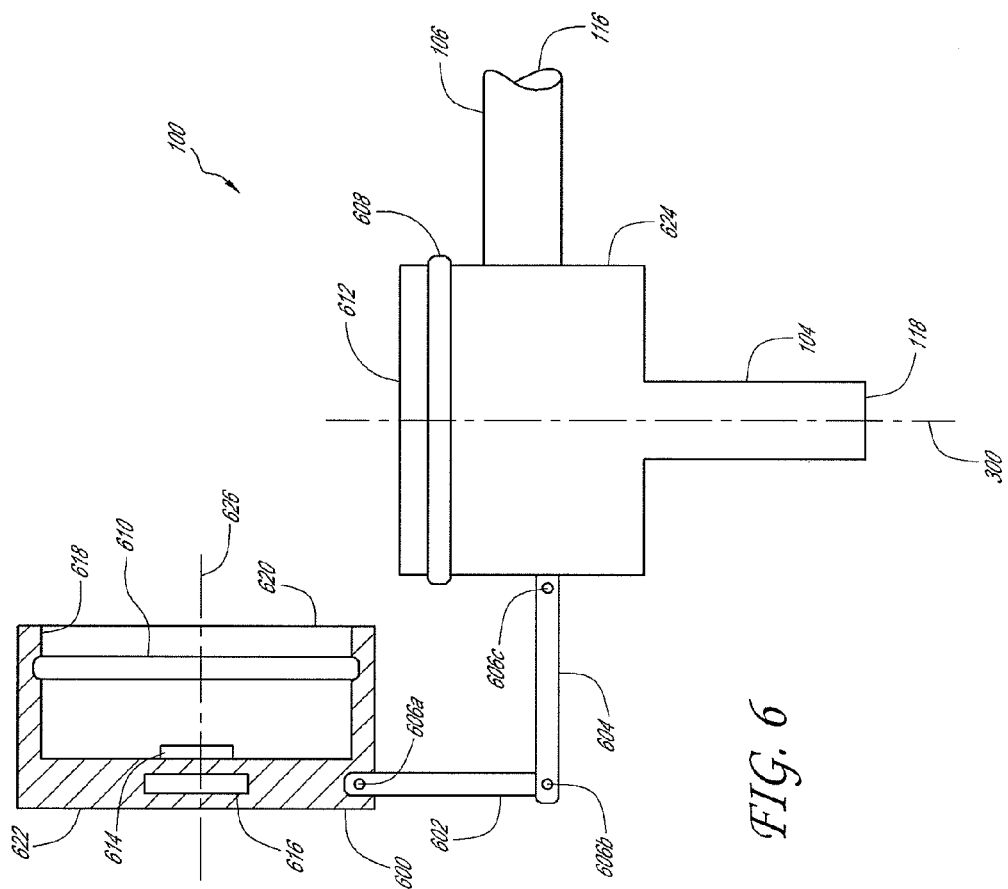
FIG. 6 is a side view of an embodiment of a self-contained illuminated infusion cannula system.

In the illustrated embodiment of FIG. 6, a cannula system 100 with a removable cap 600 is shown. The cannula system 100 can include a body 624 similar in configuration to the body 102 described in detail above, with the exception of additional features to interface with the cap 600. The removable cap 600 provides an additional means of moving the LED 616 out of or away from the accessway for the incision instrument and then coupling the LED 616 adjacent the first lumen 202 in a manner that prevents fluid 119 leakage past the LED 616 or the LED tray or housing.

The body 624 can include a proximal end 612 and a protrusion 608 adjacent the proximal end 612. The protrusion 608 can be located substantially around the periphery of the body 624 to ensure a tight equally distributed load between the cap 600 and the body 624 when the cap 600 is located or snapped over the protrusion 608. In an embodiment, the protrusion 608 can include a plurality of independent protrusions spaced circumferentially about the periphery of the body 624.

The cap 600 can include a distal end 620 and a proximal end 622, as determined when the cap 600 is attached to the body 624. The cap 600 can further include a recess 610, a lens 614, an LED 616, and a lip 618. The LED 616 is located in a central portion of the proximal end 622, substantially aligned with a cap centerline axis 626. The lens 614 can be coupled to the cap adjacent the LED 616, also substantially aligned with a cap centerline axis 626.

The lip 618 can be configured to be placed around the body 624 protrusion 608, such that the cap 600 receives the body 624. The cap 600 and the body 624 can be coupled together, the axis 626 can be substantially coaxial with the body centerline axis 300 when the cap 600 and the body 624 are coupled. The recess 610 extends substantially around an internal cavity of the cap 600, the recess being shaped to receive and interface with the protrusion 608. The fit, or dimensional tolerancing, between the cap 600 and the body 624 is sufficiently tight that when the cap 600 is coupled to the body 624, a sufficient load is distributed across the interfacing surfaces to prevent fluid 119 leakage. In an embodiment, the cap 600 is configured to be received into the proximal end 612 of the body 624 to couple the body 624 and the cap 600 together.

The cap 600 can be hinged or coupled to the body 624 via at least a pair of arms 602, 604 that can be hingedly coupled to each other. The opposing ends of the arms 602, 604 can be hingedly coupled to the cap 600 and the body 624, respectively. The arms 602, 604, cap 600, and body 624 are coupled via hinges 606a-c, which can provide relative rotation between the hinged elements about the hinge. Other hinging configurations or embodiments are possible. The hinged coupling advantageously provides the convenience of containing the cap 600 adjacent the surgical site when the cap 600 is removed from the body 624 to insert the incision instrument, or trocar. Upon completing the incision, inserting the cannula 104 into the eye 10, and removing the trocar, the cap 600 can be rotated about the hinged arms and lockingly engaged onto the body 624. The arms 602, 604 can be removed, including destructively removed, from the cap 600 and body 624 to create an open work area about the surgical site and avoid inadvertent contact with the flexible hinge.

Figure 7A:
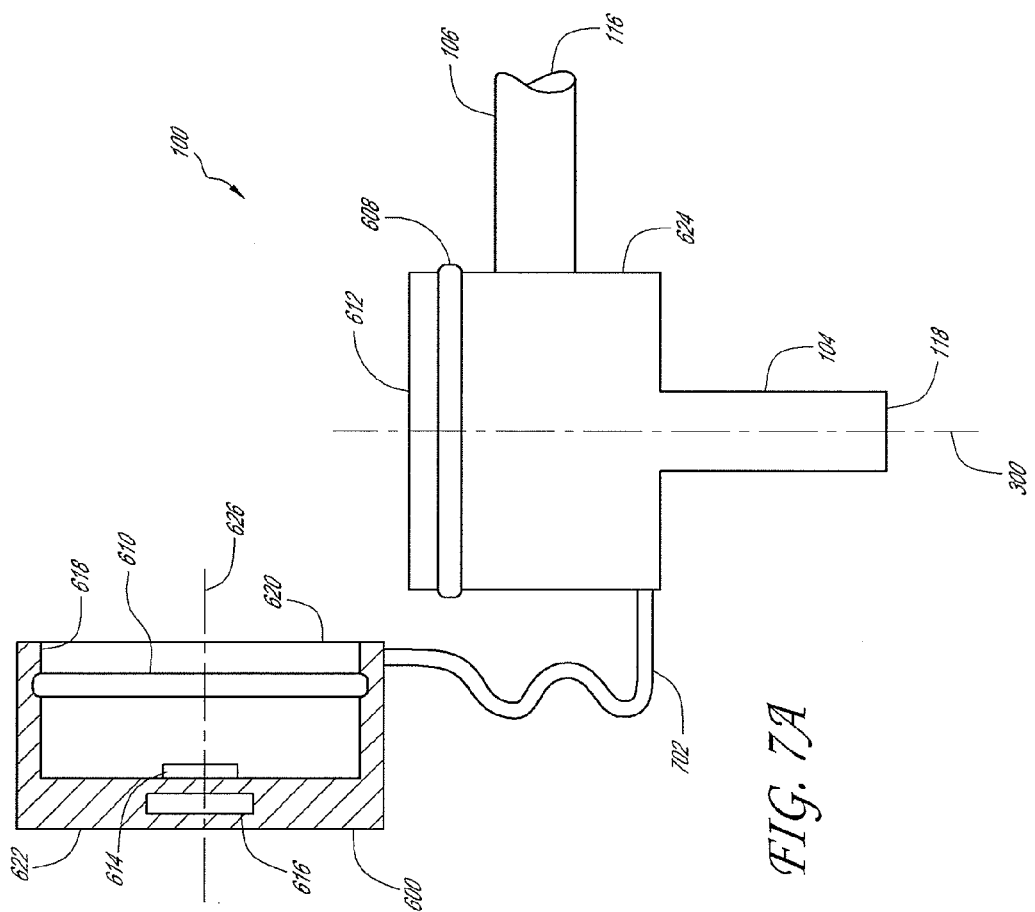
FIG. 7A is a side view of an embodiment of a self-contained illuminated infusion cannula system.

In the illustrated embodiment of FIG. 7A, the cannula system 100 with a flexible arm 702 coupling the cap 600 and the body 624 is shown. The flexible arm 702 can provide an alternative hinging mechanism between the cap 600 and the body 624. The flexible arm 702 can allow a single piece molding of the cap 600 and the body 624, whereby only the LED 616 is required to be potted into the cap 600 to define a complete cannula system 100. In an embodiment, the cap 600 and body 624 and independent pieces that are, for example, adhesively bonded to each other via the flexible arm 702. Upon cap 600 lockingly engaging the body 624 after cannula 104 insertion, the flexible arm 702 can be removed from the cap 600 and body 624 to create an open work area about the surgical site and avoid inadvertent contact with the flexible hinge.

Figure 7B:
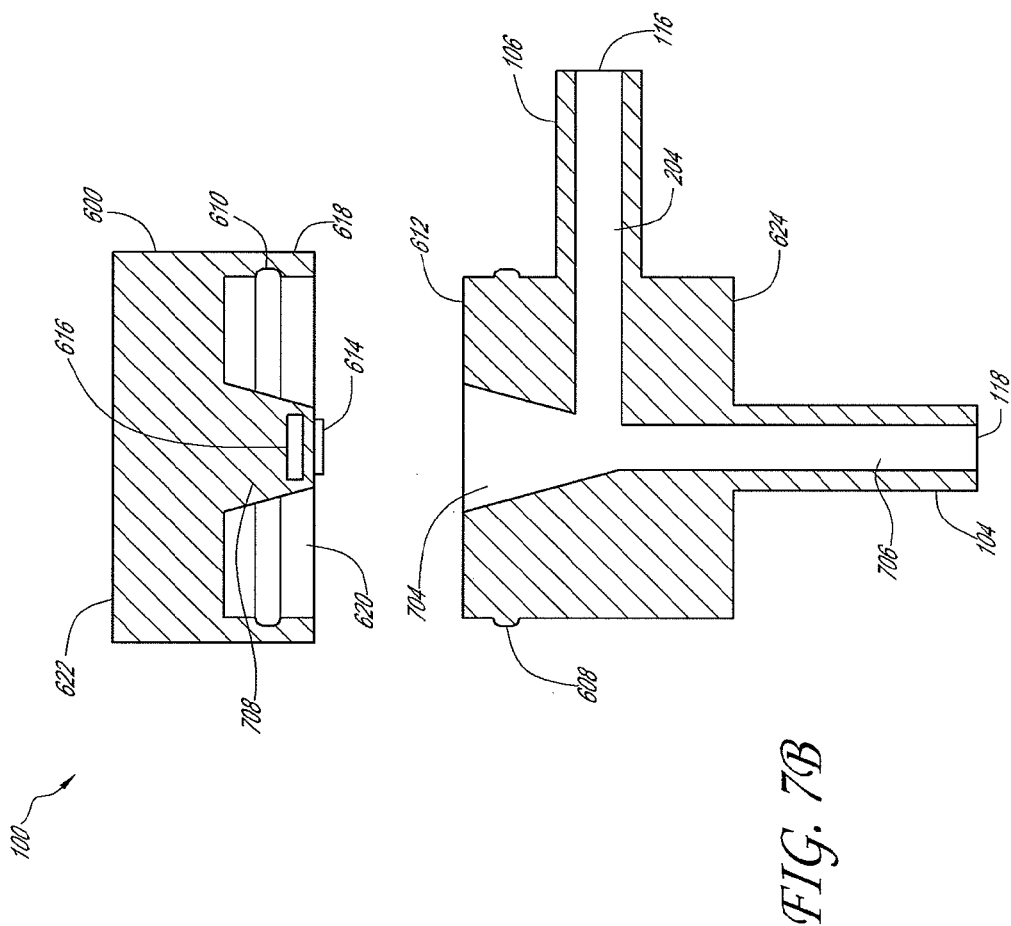
FIG. 7B is a side view of an embodiment of a self-contained illuminated infusion cannula system.

In the illustrated embodiment of FIG. 7B, the cannula system 100 with another embodiment of the cap 600 and the body 624 is shown. The cap 600 can include a cap extension 708 in the cap cavity that protrudes downward from the cap proximal end 622 toward the distal end 620. The body 624 can include first lumen 706 and the chamber 704.

The cap extension 708 can locate the LED 616, and lens 614, if applicable, closer to the junction between the first lumen 706 and the second lumen 204. The chamber 704 can be shaped to receive the cap extension 708. Placement of the LED 616 closer to the cannula outlet 118 can reduce light losses and improve the light transmittance to the eye 10. The cap 600 having cap extension 708 can be coupled to the body 624 by flexible arm 702, hinged arms 602, 604, or a functionally equivalent hinging mechanism, device, or method.

Figure 8:
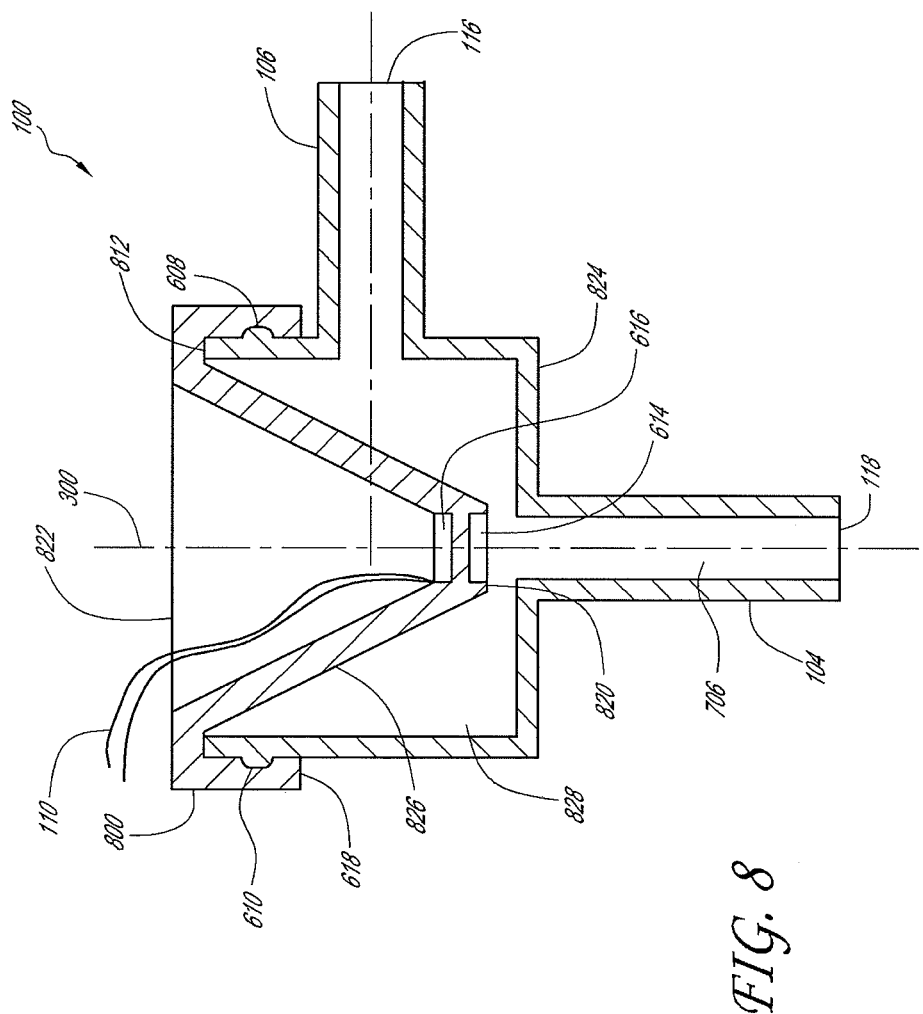
FIG. 8 is a side view of an embodiment of a self-contained illuminated infusion cannula system.
Figure 9:
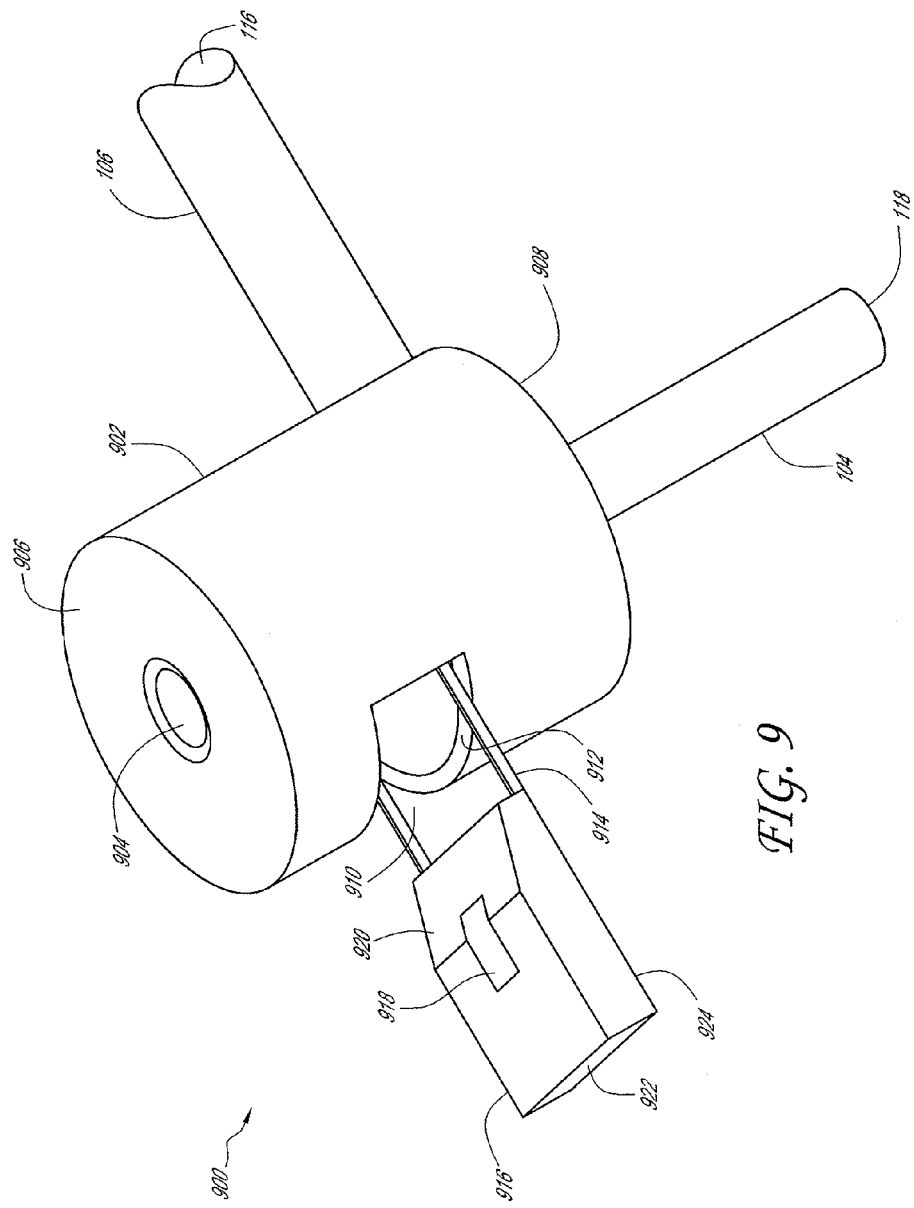
FIG. 9 is a perspective view of an embodiment of a self-contained illuminated infusion cannula system.
Figure 10:
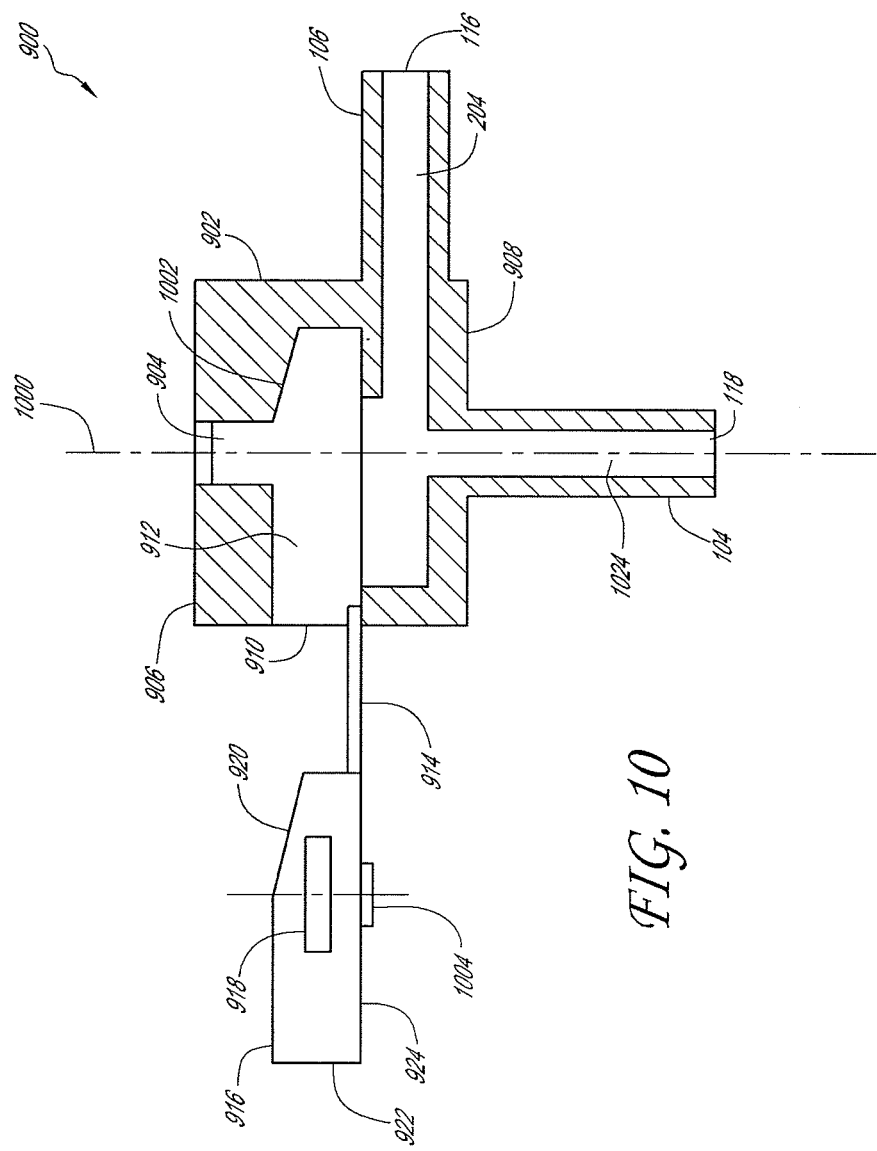
FIG. 10 is a cross-section side view of the self-contained illuminated infusion cannula system of FIG. 9.

In the illustrated embodiment of FIG. 8, the cannula system 100 is shown with a cap 800 and a body 824. The cap 800 can include a proximal end 822, a distal end 820, and a cone 826. The body 824 can include a proximal end 812 and a chamber 828. The cap 800 is similar to cap 600 except the cap 800 can include the cone 826 that extends downward away from the cap proximal end 822 and protrudes beyond the location where the fluid 119 enters the chamber 828 from conduit 106. The cone 826 can advantageously position the LED 616, and the lens 614 if applicable, below the 90 degree bend from the second lumen 204 to the chamber 828 and the first lumen 706, as illustrated in FIG. 8. Positioning the LED 616 below the second lumen 204 can place the LED downstream of the flow disturbances generated by the bend (for example, the 90 degree bend), and can reduce the likelihood of the flow causing loss of light 109 transmittance and/or shadows in the light.

The chamber 828, as illustrated in FIG. 8, can include almost the entire internal volume of the body 824. In an embodiment, the chamber 828 can include any geometry similar to, or equivalent to, the chamber geometries described above, provided the cone 826 is compatible and can interface the various geometries when the cap 800 is lockingly engaged with the body 824.

In the illustrated embodiment of FIGS. 9-13, an embodiment of a cannula system 900 is shown. The cannula system 900 can provide for a second aperture 910 positioned on the periphery of a body 902 that allows lateral movement of the LED 918 away from a centerline axis 1000. The lateral movement of the LED 918 can establish access through a first lumen 1024 for the incision instrument, or trocar. The LED 918 can then be urged laterally to lockingly engage and establish a fluid seal with the body 902.

The body 902 can include a distal end 908 and a proximal end 906. A first aperture 904 can be positioned adjacent the proximal surface at the proximal end 906. The first aperture 904 can open to a first lumen 1024 that extends the full length of the body 902 and the cannula 104. The second aperture 910 can define an opening into the body 902, the opening defining a chamber 912. The chamber 912 can be configured to receive an insert or LED tray/housing 916. The chamber 912 can include a tapered surface 1002 on a proximal surface of the chamber 912. The tapered surface 1002 can define a decreasing thickness, or longitudinal height, of the chamber 912 as the second aperture 910 extends further away from the opening of the second aperture 910. The decreasing height of the chamber 912 can define a wedge-like feature that lockingly receives a similarly shaped end of the insert or LED tray/housing 916. The wedge shape can force the insert 916 distally, creating downward forces, and can create a fluid seal between a bottom face 924 of the insert 916 and a distal surface of the chamber 912. In an embodiment, the sealing function can be provided by any acceptable means, for example, a tightly toleranced dimensional fit between the insert 916 and the chamber 912, a biologically compatible sealing material between the insert 916 and the chamber 912, e.g. a seal, a gasket, a viscous lubricant, or the like, or other suitable means.

The insert 916, as illustrated in FIGS. 9-13, can include the bottom face 924, a front face 922, an LED 918 in a cavity, and a top tapered surface 920. In an embodiment, a lens 1004 can be coupled to or adjacent the bottom face 924. The tapered surface 920 can include a taper angle θ, that can be between about 0.25 degrees and about 10 degrees, more preferably between about 0.75 degrees and about 3 degrees. In an embodiment, the top tapered surface 920 can taper across any lateral length, which can correspondingly vary the wedge contact surface and the downward distally directed fluid sealing force distribution.

The body 902 and the insert 916 can be coupled by a pair of connector members 914. The connector members can provide for a single piece integrally molded assembly of the cannula system 900. Upon removal of the trocar from the cannula system, the connector members 914 can be decoupled at the insert 916. The surgeon can use instruments, such as a pair of forceps, to urge the insert 916 into the aperture 910 and chamber 912. The connector members 914 can provide an additional locking mechanism, in addition to the tapered wedge locking feature, to retain the insert 916 in the chamber 912. The locking mechanism of connector members 914 can also prevent removal of the insert 916 such that the cannula system 900 can only be a single use medical device system.

Figure 14:
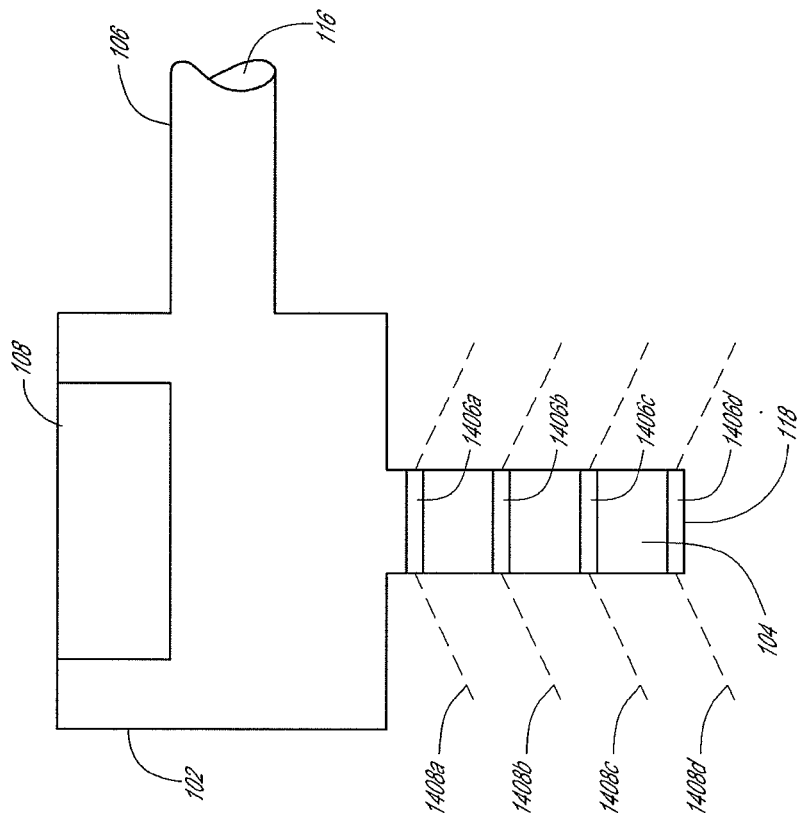
FIG. 14 is a side view of an embodiment of a self-contained illuminated infusion cannula system.
Figure 15:
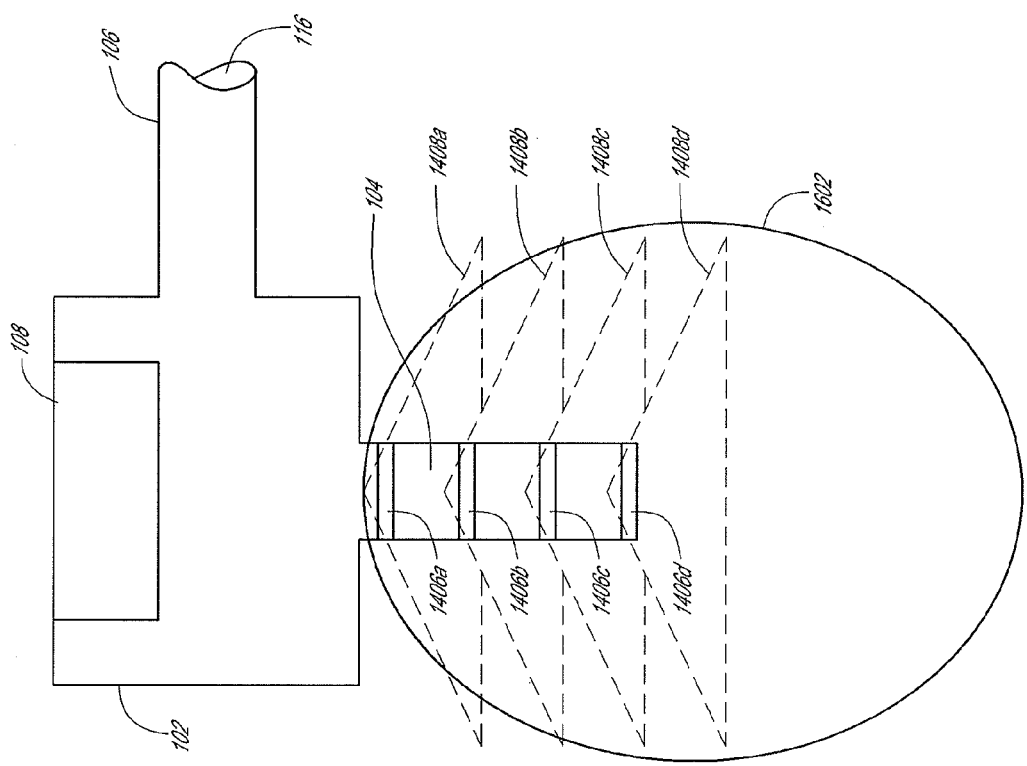
FIG. 15 is a side view of the self-contained illuminated infusion cannula system of FIG. 14 showing an improved field of view.

In the illustrated embodiment of FIGS. 14-17, embodiments of a cannula system 100 having varying optical elements coupled to the cannula, are shown. As illustrated in FIGS. 14 and 15, the dispersion of the light 109, and thus the field of view at the surgical site, can be selectively controlled by the geometry, transparency, and materials included in fabricating a cannula 104. Optical elements 1406a-d can be fabricated into the cannula 104. The optical elements 1406a-d can be devices such as prisms, lenses, filters, or the like. The optical elements 1406a-d, as illustrated in FIGS. 14 and 15, can extend circumferentially for at least a portion of the cannula 104 outer diameter. The optical elements can be fabricated and/or oriented to disperse at predetermined angles 1408a-d, and spaced longitudinally along a centerline axis of the cannula 104 to obtain predetermined coverage for the field of view 1602, shown, for example, in FIG. 15. In an embodiment, the predetermined angles 1408a-d can be the same or substantially the same, all different or substantially different, or any combination thereof, to define the field of view 1602.

Figure 16:
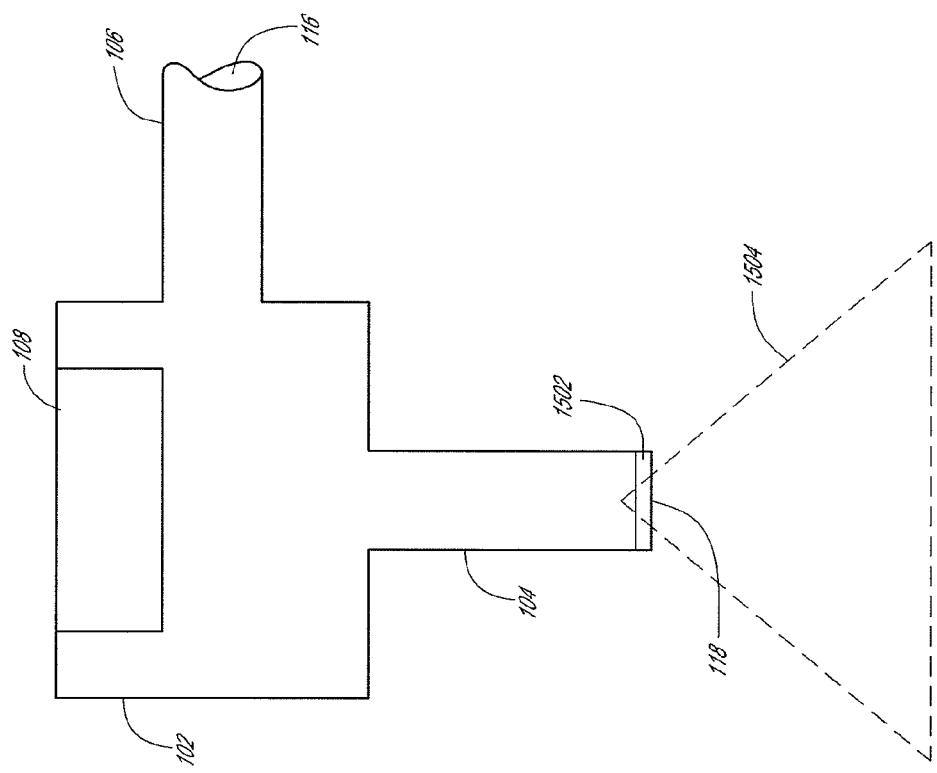
FIG. 16 is a side view of an embodiment of a self-contained illuminated infusion cannula system.
Figure 17:
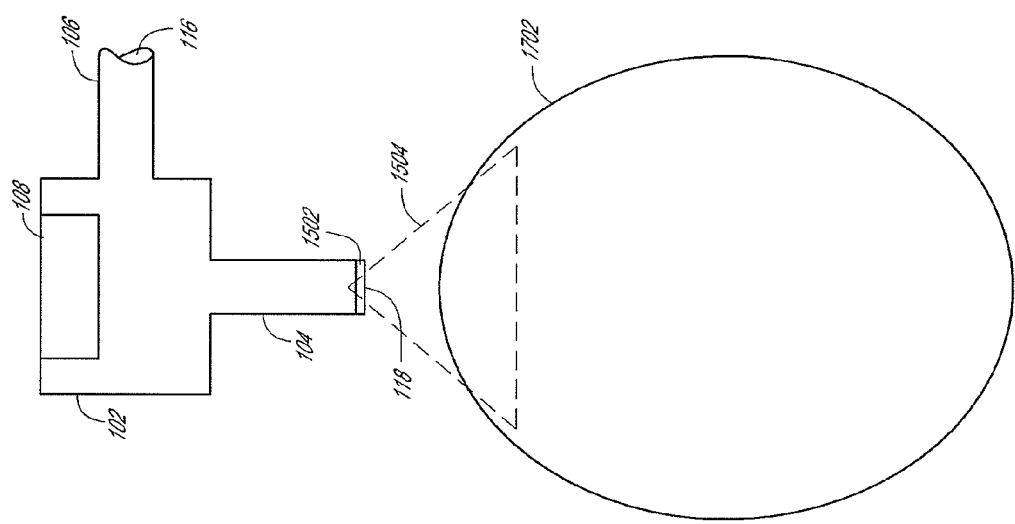
FIG. 17 is a side view of the self-contained illuminated infusion cannula system of FIG. 16 showing a reduced field of view.

With reference to FIGS. 16 and 17, a cannula 104 having optical element 1502 located at the cannula outlet 118 is shown. The cannula 104 can have a single optical element, for example a prism can extend circumferentially around the full outer diameter of the cannula 104. The dispersion beam angle can define the beam area and ultimately the field of view 1702. Comparison of field of views 1602, 1702 can indicate the variation in illumination capability, including depth and width, dependent upon the optical element parameters, characteristics, and quantity. Cannula 104 can include prisms having a greater dispersion angle relative to the cannula outer diameter and can include a greater number of prisms coupled to the cannula. The resulting field of view 1602 can be significantly larger than the field of view 1702, which can have a smaller dispersion angle 1504 and only a single prism 1502 located at the distal end of the cannula 104.

Figure 18:
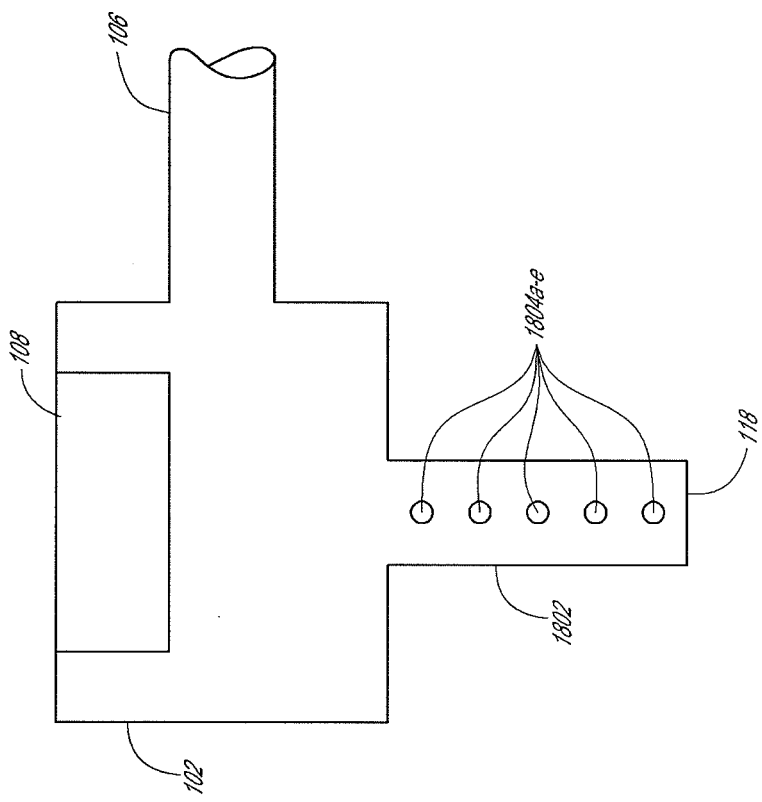
FIG. 18 is a side view of an embodiment of a self-contained illuminated infusion cannula system.

With reference to FIG. 18, an embodiment of a cannula 1802 is shown. The cannula 1802 is similar to the cannula embodiments described above except the cannula 1802 can include a plurality of fluid apertures 1804a-e. The fluid apertures 1804 can be spaced longitudinally and circumferentially, and can provide apertures at various depths in the eye 10 and at various angles relative to a longitudinal axis. The fluid apertures 1804 can provide exit outlets for the infusion fluid 119 to irrigate and provide intraocular pressure to the eye 10. The fluid apertures 1804 can evenly distribute the infusion fluid 119 and avoid delivery of the fluid 119 to only a local portion of the vitreous cavity of the eye 10. In an embodiment, the fluid apertures 1804 can transmit light 109 at predetermined angles and longitudinal locations.

Figure 19:
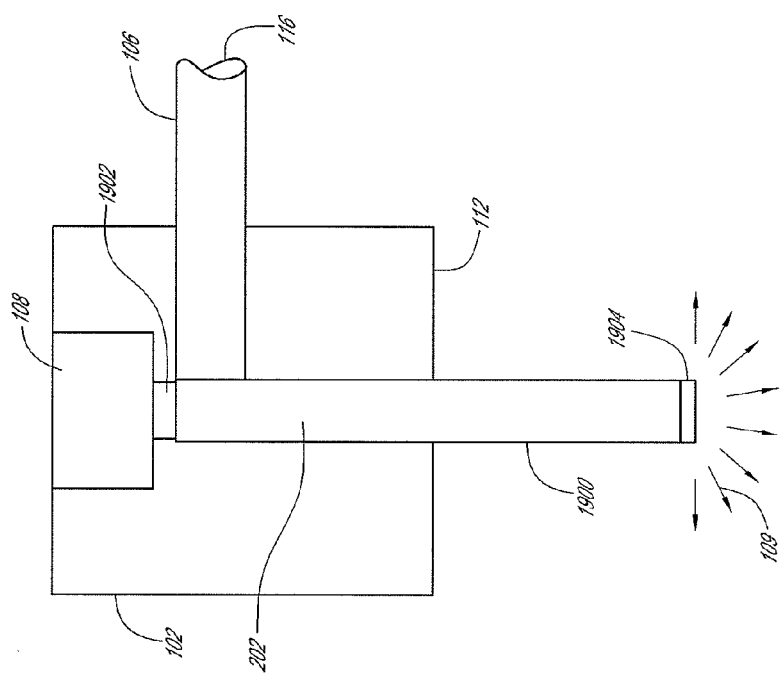
FIG. 19 is a side view of an embodiment of a self-contained illuminated infusion cannula system.

With reference to FIG. 19, an embodiment of a cannula system 100 that can have a cannula 1900 is shown. The cannula 1900 can include at least a portion of the distal tip 1904 that can include a phosphorescence material applied or coupled to the surface and/or embedded in the transparent material. The cannula system 100 can further include an optical element 1902 that can selectively disperse wavelengths of light 109, and the wavelengths associated energy. The optical element can further collimate the selectively disperse wavelengths to facilitated transmittance through the full length of the cannula 1900. The selective wavelengths transmit through, and the wavelength energy excites, the phosphorescence material located on the cannula 1900. The tip generates divergent relaxation wavelength lights and illuminates the surgical sight. The illuminated light can result in an intraocular illumination with relatively high intensity.

In an embodiment of the cannula system illustrated in FIG. 19, the light source system can be a light emitting diode system that can generate white light, or so-called warm white light. The light emitting diode system can comprise a light emitting diode, generating blue light, wherein the tip and/or wall of the optical bus is coated with a phosphorous layer. When the divergent blue light hits on the phosphorous chemical in the coating layer, this layer in turn generates a greenish and yellowish light accompanied with the original bluish light, and the light generated by the light emitting diode system can be whitish depending on the contribution of the blue, green, and yellow lights.

In an embodiment of the cannula system illustrated in FIG. 19, the light source system, disclosed herein, can be a laser diode system that can generate white light. The laser diode system can comprise a laser diode, generating blue light, wherein the tip and/or wall of the optical bus is coated with a phosphorous layer. When the divergent blue light hits on the phosphorous chemical in the coating layer, this layer can generate a greenish and/or yellowish light accompanied with the original bluish light, and the light generated by the laser diode system can be whitish depending on the contribution of the blue, green, and/or yellow lights.

The use of lenses to disperse a specific wavelength bandwidth can be combined with multiple LEDs for selective colorization and tint of an illuminated area. Independent LED power control can give the surgeon illumination options for various surgical procedure needs. The use of bandwidth limited wavelength light allows physicians to operate with improved contrast for visualization of specific structures in the eye. Additional features include controlling not only the intensity, but also the quality of the light, which is improved by changing the color, or color temperature, of the light from the light source via a filter device, with the light produced from one or more sources. Further details regarding these bandwidth limited light and light coloration modifying devices, systems, and methods for providing illumination are shown and described in U.S. Pat. No. 7,654,716 and in U.S. Publication 2009-0146583, and the entirety of both are incorporated by reference herein and form a part of this specification.

Figure 20:
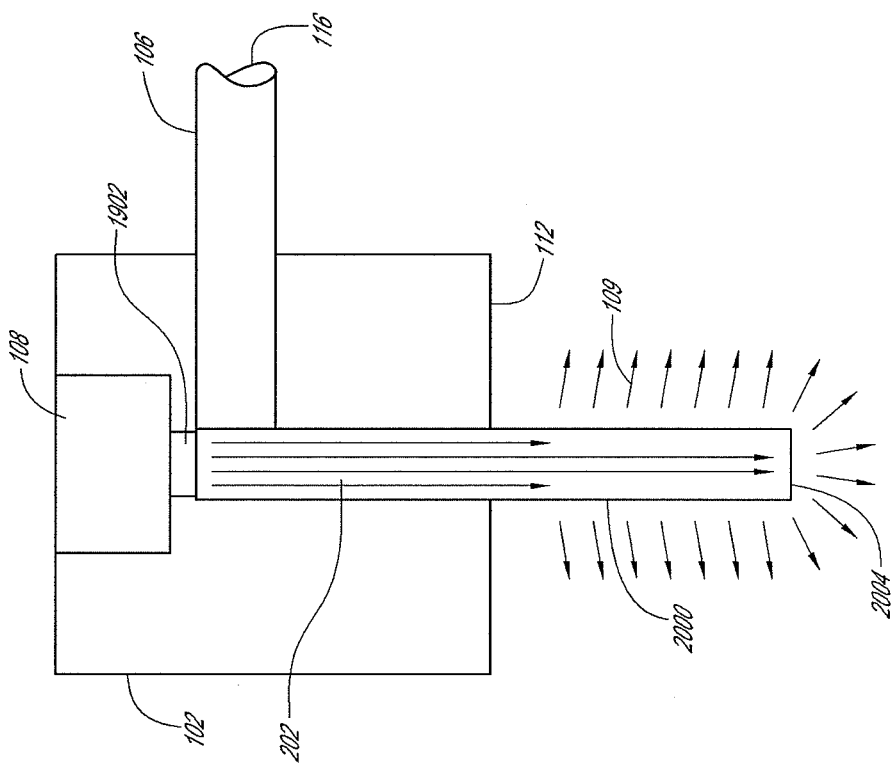
FIG. 20 is a side view of an embodiment of a self-contained illuminated infusion cannula system.

With reference to FIG. 20, a cannula system 100 with a cannula 2000 is shown. The cannula system is similar to the system illustrated in FIG. 19, except the cannula 2000 can include a phosphorescence material applied or coupled to the surface and/or embedded in the transparent material along the full length of the cannula 2000 from the distal end 112 of body 102 to the distal end 2004 of the cannula 2000.

Figure 21A:
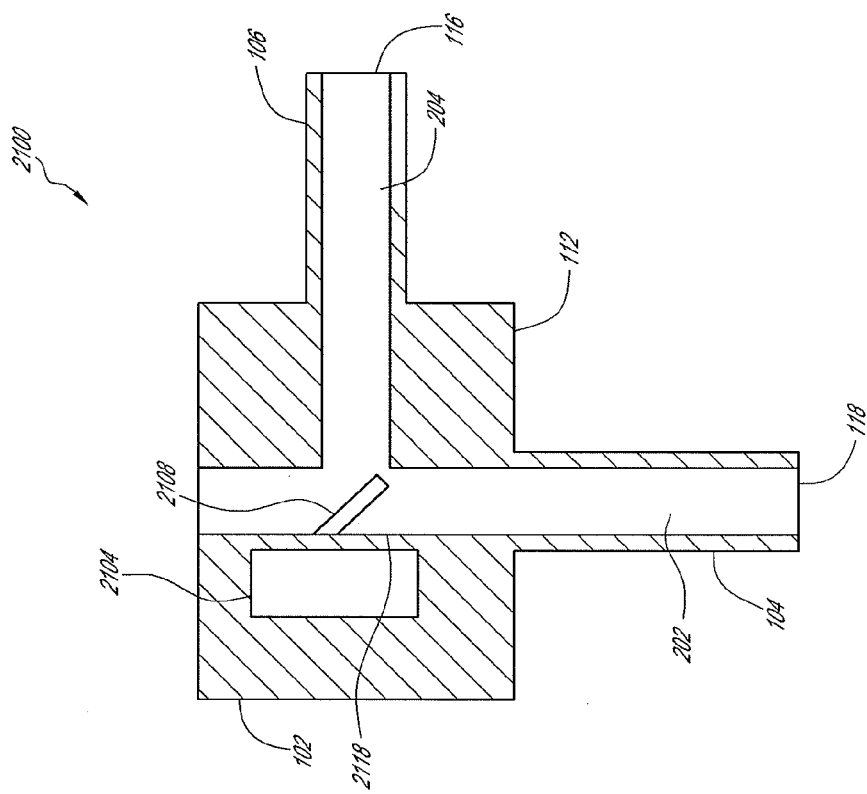
FIG. 21A is a side view of an embodiment of a self-contained illuminated infusion cannula system.
Figure 21B:
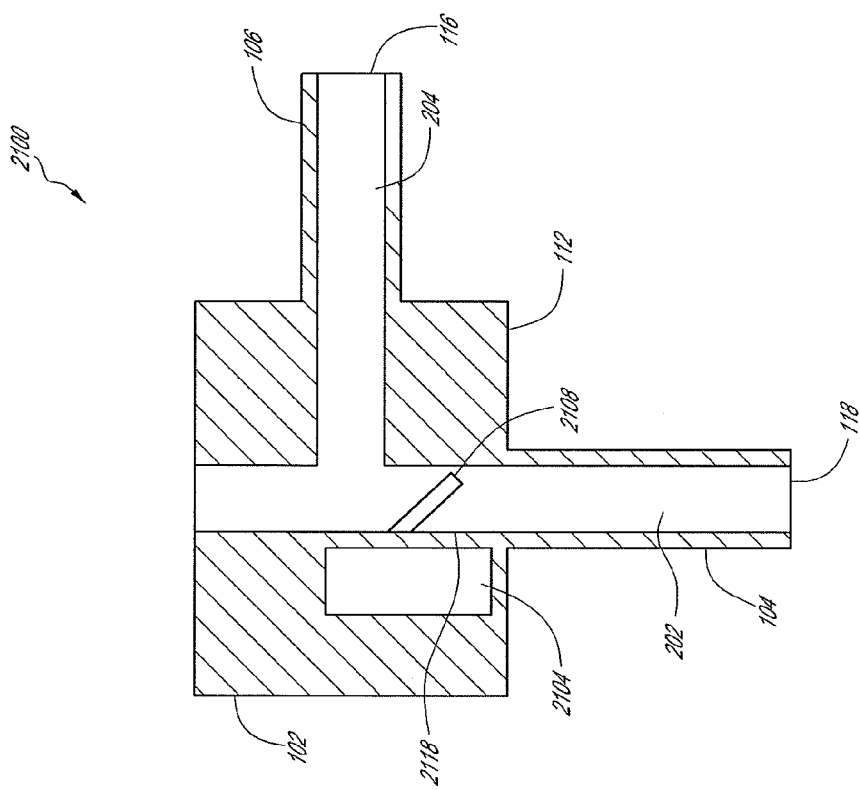
FIG. 21B is a side view of an embodiment of a self-contained illuminated infusion cannula system.

With reference to FIGS. 21A and 21B, a cannula system 2100 is shown with an LED 2104 offset to the side of the first lumen 202. The majority of the cannula system 2100 is similar to the cannula systems described above, except for the location of the LED 2104, the location and configuration of an optical element 2108, and the length of the first lumen 202. The LED 2104 can extend lengthwise, parallel to the first lumen 202. The position of the LED 2104 off to the side of the body 102 can negate the need to move the LED 2104 out of the first lumen 202 to provide a passage for the incision instrument or trocar. Thus, the embodiment illustrated in FIGS. 21A and 21B can simplify creation of the incision.

The LED position adjacent the first lumen 202 can direct the light transmitted from the LED across laterally through the first lumen 202 rather than distally toward the eye 10. The optical element 2108 can redirect, filter, magnify, or the like, the light 109 from the lateral direction to be directed distally through the first lumen 202 toward the eye 10. The optical element 2108 can be springingly coupled to a window 2118 defined by a thin transparent portion of the body 102 that can be positioned between the LED 2104 and the first lumen 202. The resilient spring-like, spring-loaded characteristic of the optical element 2108 can provide for temporary displacement of the optical element 2108 adjacent the sidewall of the first lumen 202 while the trocar is inserted through the first lumen 202. Thus, the optical element 2108, the first lumen 202, and the trocar can be sized such that the optical element and the trocar can movingly fit relative each other within the first lumen 202.

The LED 2104 position illustrated in FIG. 21B can be advantageously located in the optical element 2108 downstream of the 90 degree bend through which the fluid 119 passes in transitioning from the second lumen 204 to the first lumen 202. The downstream position places the optical element 2108 substantially beyond the greatest flow disturbances generated by the flow around the 90 degree bend between the two lumens.

Figure 21C:
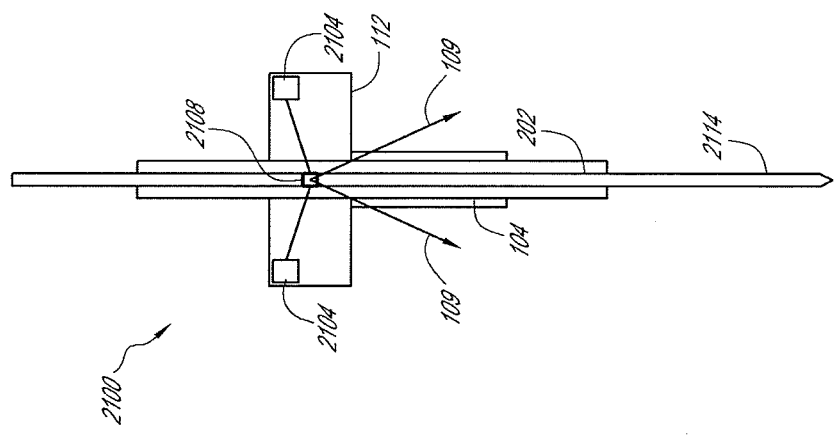
FIG. 21C is a side view of an embodiment of a self-contained illuminated infusion cannula system.

In the illustrated embodiment of FIG. 21C, a cannula system 2100 is shown with at least two LEDs 2104 offset to the side of the first lumen 202. The cannula system of FIG. 21C is similar to the cannula system of FIGS. 21A and 21B except that there is more than one LED positioned in the body 102. The arrangement to redirect the lateral transmittance of the LEDs is also similar. Having more than one LED can allow each LED to be positioned slightly offset in the longitudinal direction from the first lumen 202. This can provide dimensional clearance for the one or more optical elements to project light into the first lumen 202. In an embodiment, the plurality of LEDs can have the individual light 109 transmittance directed to a single optical element that will redirect the combined light 109 from the LEDs through the first lumen 202 toward the eye 10.

The position of the LEDs 2104 to the sides of the body 102 can also negate the need to move the LED(s) 2104 out of the first lumen 202 to provide a passage for the incision instrument or trocar 2114.

The multiple LEDs 2104 can include LEDs of various colors, such as blue, red, yellow, and white. The multiple LEDs 2104 of different colors can be provided on separate individual dies, or can include different color LEDs on a single die. These LED light sources can provide an optical signal/output for illumination in a band of specific wavelengths. The different sources, red, green, blue, white, etc., can be configured in a designated pattern for maximum light output efficiency. One of the advantages of using this configuration is that by controlling the current to the LED, the output light can be tuned to various intensities. This can allow for better safety, visualization, and illumination that is tunable to individual cases and surgeons. In addition, the variation in light of different spectrum from the outputs of the LEDs 2104 can allow for improved contrast ratios for surgical illumination.

In some embodiments, an illumination system can use multiple LED 2104 sources to provide increased flux strength for illumination. The multiple LEDs 2104 can be arranged in desired configurations about the first lumen 202, such as equally spaced circumferentially, hex, line, chandelier, or the like. The entire visible spectrum of the LED 2104 light source wavelength optical output is usable. Additionally, the optical intensities of the LEDs 2104 are easily tunable with the input current.

Light produced by the LEDs can be dispersed through the lens 2108. The lens 2108 can be made using any suitable materials and/or shapes. Further, any suitable configuration, e.g., thin film, Fabry-Perot, or the like, and/or material can be used for a filter applied to the light 109 dispersed from the LED 2104. One or more lenses can provide optional magnification, collimation, or focusing within the first lumen 202. Further details are provided in application Ser. No. 12/237,110, filed Sep. 24, 2008, incorporated by reference above.

Figure 22:
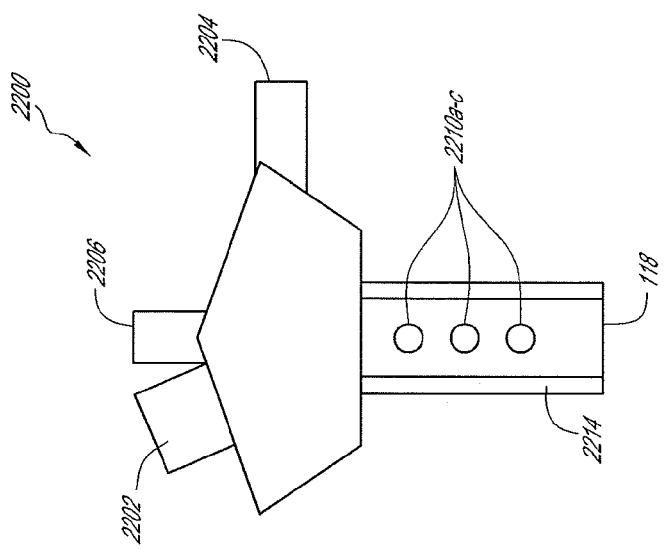
FIG. 22 is a side view of an embodiment of a self-contained illuminated infusion cannula system.

With reference to FIG. 22, an embodiment of a cannula system 2200 is shown. The cannula system 2200 includes two fluid infusion ports 2204, 2206, and offset externally positioned LED 2202 light source, a phosphorescence coated or embedded material cannula 2214, and fluid apertures 2210a-c. The cannula system 2200 provides an additional embodiment that can selectively disperse the LED 2202 light wavelengths such that the desired energy is transmitted to the phosphorescence coated or embedded cannula 2214 to excite the material and advantageously illuminate surgical site in or adjacent to the eye 10. The fluid apertures 2210a-c can provide infusion flow outlets to evenly deliver the infusion fluid 119 about the surgical site.

Figure 23:
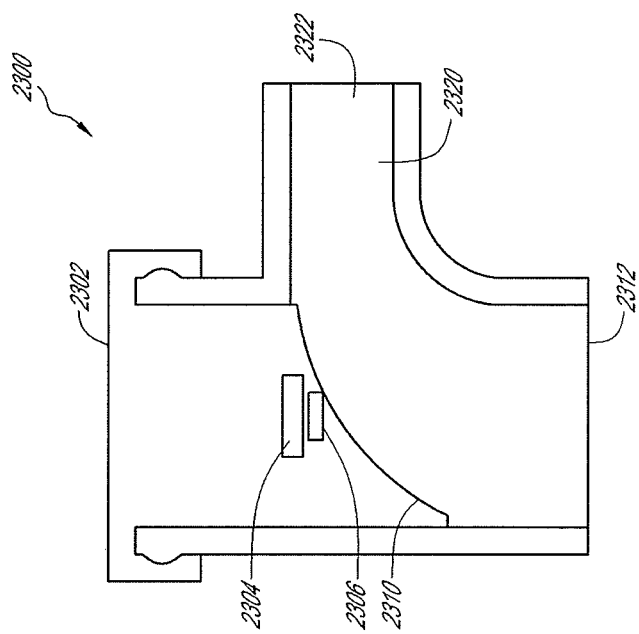
FIG. 23 is a side view of an embodiment of a self-contained illuminated infusion cannula system.
Figure 24:
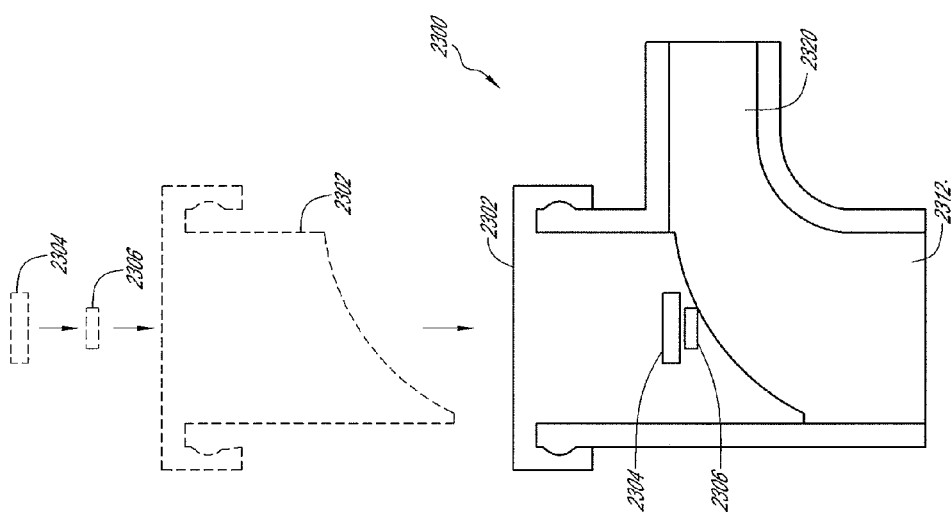
FIG. 24 is a side view of the self-contained illuminated infusion cannula system of FIG. 23.

With reference to FIGS. 23 and 24, a cannula system 2300 is shown. The cannula system 2300 is similar to the cannula systems described above except that the 90 degree bend can be provided with a generous transition radius rather than a sharp 90 degree bend transition. The generous transition radius can advantageously reduce the flow disturbances that are adjacent to a LED 2304 and a lens 2306, if the optional lens is implemented in the embodiment. At least a portion of the flow bend transition radius 2310 can be fabricated as part of a modular cap 2302, similar to the caps described above. Fabricating the radiused surface on an external surface of a separate piece of the cannula system can simplify the fabrication of the body. The transition radius illustrated in FIGS. 23 and 24 shows the inner diameter of the second lumen 2320/2322 having a smaller magnitude than the inner diameter of the first lumen 2312.

Figure 25:
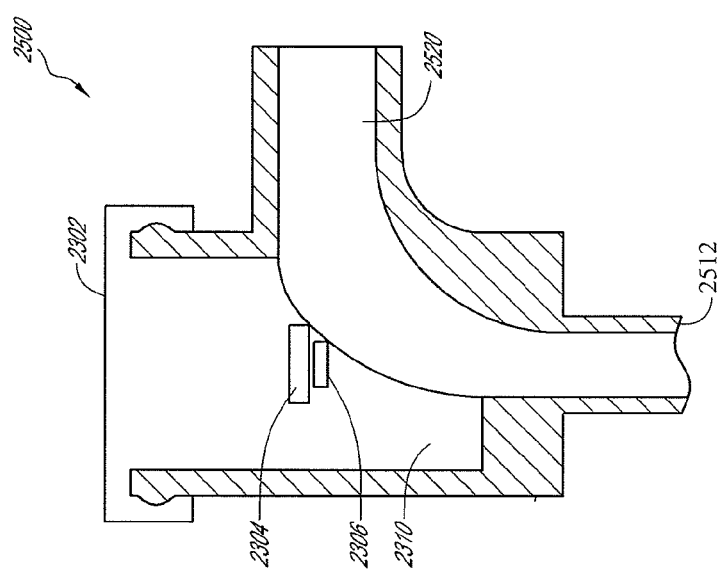
FIG. 25 is a side view of an embodiment of a self-contained illuminated infusion cannula system.

With reference to FIG. 25, a cannula system 2500 is shown. The cannula system 2500 is similar to the cannula system 2300 shown in FIGS. 23 and 24 except the inner diameter of the second lumen 2520 can have a larger magnitude than the inner diameter of the first lumen 2512.

Figure 26:
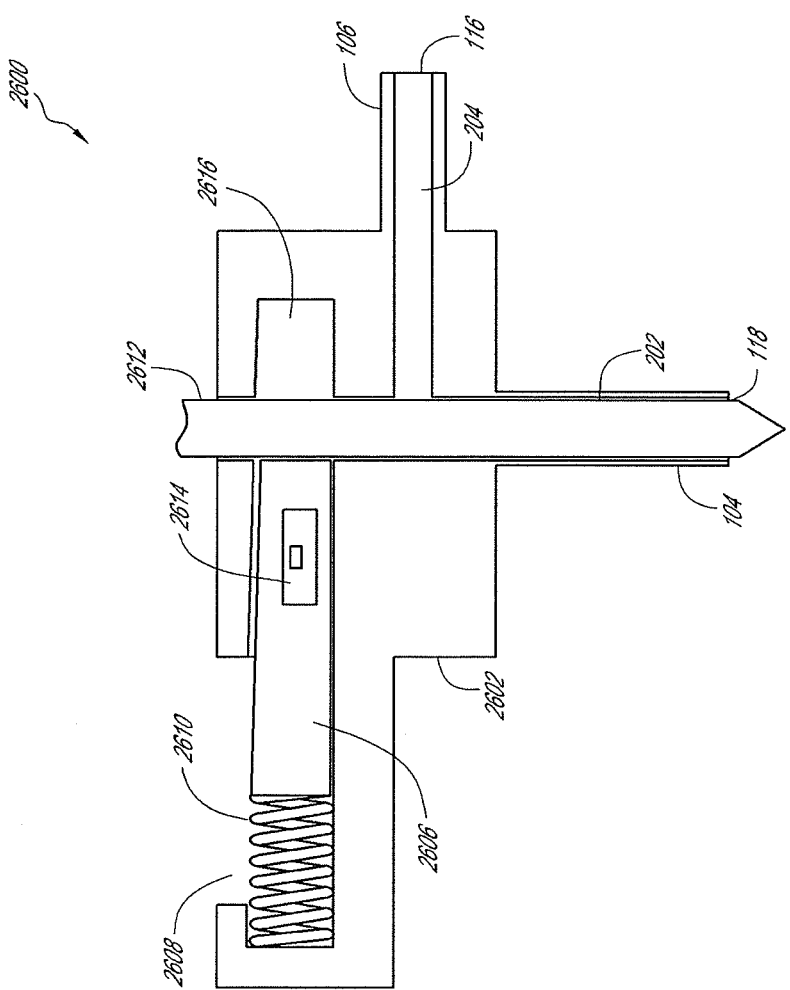
FIG. 26 is a side view of an embodiment of a self-contained illuminated infusion cannula system.

With reference to FIG. 26, a cannula system 2600 is shown. The cannula system 2600 is similar to the cannula systems described above except for the following features. The cannula system can include a body 2602, a cannula 104, and a chamber 2616, and an opening 2608. The cannula system can comprise a LED tray 2606 that is configured to slide laterally to allow instruments to pass through the cannula 104. The LED tray 2606 can be configured to move from a first closed position to a second opened position. The cannula 104 can define at least a portion of a first lumen 202 that can receive a trocar 2612, as illustrated in FIG. 26. In an embodiment, the cannula system is prepackaged with a trocar positioned within the lumen 202 such that the LED tray 2606 is in the second opened position. After the trocar is used to make an incision in the eye, the trocar can be removed from the cannula 104, thereby allowing the LED tray 2606 to move laterally into the first closed position. Alternatively, the cannula 104 is not prepackaged with a trocar positioned within the cannula. In an embodiment, a trocar can be inserted into the cannula 104. As the trocar is inserted into the cannula 104 the distal end of the trocar can be configured to engage a tapered surface of the LED tray 2606 to urge the LED tray 2606 laterally to open the cannula 104 thereby allowing the trocar to pass through. The chamber 2616 can have a tapered proximal surface to define a wedge like feature as described above in detail in reference to FIGS. 9-13.

The cannula system 2600 can further include the LED tray 2606, an LED 2614, and a resilient member, or spring 2610. In an embodiment, any suitable resilient material can be included in the cannula system 2600. The spring can be positioned to a lateral side adjacent the opening 2608. The opening 2608 can provide access to the LED tray 2606 and the spring 2610. The access through the opening 2608 can provide for the LED 2614 to be potted into the LED tray 2606. The chamber 2616 can receive the LED tray 2606, whereupon the LED tray 2606 can be urged to a lateral side against the resistance of spring 2610 and away from the first lumen 202 to allow the trocar 2612 to pass through the first lumen 202.

With continued reference to FIG. 26, the LED tray 2606 can include a tapered top, or proximal, surface to define a corresponding wedge shaped feature for sliding interaction with the tapered surface of the chamber 2616. Removal of the trocar 2612 upon insertion of the cannula 104 into the sclera 14 provides for the spring to urge the LED tray 2606 adjacent the tapered surface of the chamber 2616. The LED tray 2606 is urged such that the LED 2614 is substantially aligned to transmit light 109 distally through the first lumen 202 into the vitreous cavity of the eye 10. In an embodiment, the LED tray 2606 forms a seal with the side walls of the lumen 202. To further ensure a tight seal, the tapered surfaces of the LED tray 2606 and the chamber 2616 can be configured to provide counter forces that help ensure a tight seal. In an embodiment, the LED tray 2606 is positioned above the second lumen 204, thereby allowing the force of the entering infusion fluid to further push or urge the LED tray 2606 upward or proximally to form a tighter seal to prevent fluid from exiting the body 2602.

In an embodiment, the LED tray 2606 can pivot about an end of the tray, rather than laterally slidable as described above. The tray can pivot about an end that is coupled to a portion of the chamber 2616. The free end, or any portion of the LED tray 2606, can be resiliently coupled to a portion of the chamber 2616. Accordingly, the LED tray 2606 can pivot into and out of the first lumen 202 with resilient resistance provided by a suitable resilient member or spring 2610. A trocar can be inserted and removed, urging aside and releasably positioning the LED tray 2606 adjacent the first lumen 202 in the process. The LED tray 2606 can be configured to pivot in any suitable direction that can place the LED tray adjacent the first lumen 202 for directing the light 109 out through cannula 104, e.g., laterally, axially, or the like. Accordingly, the LED tray can be configured to move from a normal, at rest, first position to a second position as the trocar is inserted into the first lumen 202, thereby allowing the trocar to pass through the lumen 202. When in the first position, the LED tray 2606 can be urged into a lateral position or a position that is perpendicular to the longitudinal axis of the lumen 202. In an embodiment, the LED tray 2606 forms a seal with the side walls of the lumen 202. To further ensure a tight seal, the side walls of the lumen 202 can have a lip to interface with the LED tray 2606. In an embodiment, the LED tray 2606 is positioned above the second lumen 204, thereby allowing the force of the entering infusion fluid to further push or urge the LED tray 2606 upward or proximally to form a tighter seal to prevent fluid from exiting the body 2602.

The above described details are combined and configured to provide a self contained illuminated infusion cannula that can readily positions, and is capable of readily repositioning, a medical implant at a desired location within a patient. The sclera incision, cannula insertion, incision instrument removal, and light transmittance to the vitreous cavity of the eye 10 is described with reference to FIG. 26 below, however the steps accordingly describe the implementation of any of the cannula systems described above during ophthalmic surgical procedures.

The cannula system 2600 can include assembling the LED 2614 into the LED tray 2606. The LED 2614 can be coupled to the tray 2606 by potting the LED into an LED cavity within the tray, and locating the LED adjacent a transparent window for transmitting light 109 through the first lumen 202. Assembling the cannula system 2600 can include placing a trocar 2612 and extending it through, and out, the distal end of the cannula 104. The inserting of the trocar through the cannula 104 and thus, the first lumen 202, advantageously urges the LED tray 2606, laterally moving the tray 2606 in the direction toward and against the resilience of the spring 2610.

The sharpened tip of the trocar 2612 can be aligned with the desired incision, or insertion, location on the sclera 14 of the eye 10 that is suitable to illuminate the surgical site within the vitreous cavity. Locating the cannula 104 and the trocar 2612 adjacent and substantially normal, or any suitable angle of entry for the trocar 2612, the cannula 104 and body 2602 is statically positioned. Urging the trocar 2612 through the statically positioned body 2602 and cannula 104, the sharpened distal tip of the trocar 2612 penetrates the sclera, creating a suitable passage for the cannula 104. The trocar can then be held statically positioned in the course of urging the body 2602 toward the outer surface of the sclera and concurrently urging the cannula 104 through the incision created by the trocar 2612. The cannula 104 slides distally about the statically positioned trocar 2612. The elastic nature of the sclera 14 forms a sealing engagement about the cannula 104 to prevent leakage of vitreous fluid, infusion fluid, or the like.

The trocar 2612 can be removed from the cannula system 2600 by proximally urging and sliding the trocar outward away from the eye 10 and out of the first lumen 202. Removing the trocar 2612 allows the LED tray 2606 to releasably and slidably enter the chamber 2616. The resiliency of the spring 2610 is configured to laterally move or suitably position the LED light transmittance portion over, or adjacent, the first lumen 202.

Urging of the LED tray 2606 into the wedge receiving geometry of the chamber 2616 generates fluid sealing downward forces between the LED tray 2606 and the distal surfaces of the chamber 2616. The opening 2608 provides access to supply additional locating loads against the LED tray 2606 to assist the spring 2610 and facilitate suitable location of the LED 2614 about the first lumen 202. The cannula 104 can be adjusted by positioning the cannula system into a suitable arrangement and orientation adjacent the outer surface of the sclera 14 as well as in the vitreous cavity of the eye 10.

Providing power to the LED transmits light 109 out of the LED 2614 and the LED tray 2606. The light 109 is transmitted, or permitted to pass, distally through the first lumen 202 into the vitreous cavity of the eye 10. Modifying the power source provided to the LED 2614 can vary the light transmittance to the surgical site according to a suitable illumination within the vitreous cavity and adjacent the eye 10.

Figure 27:
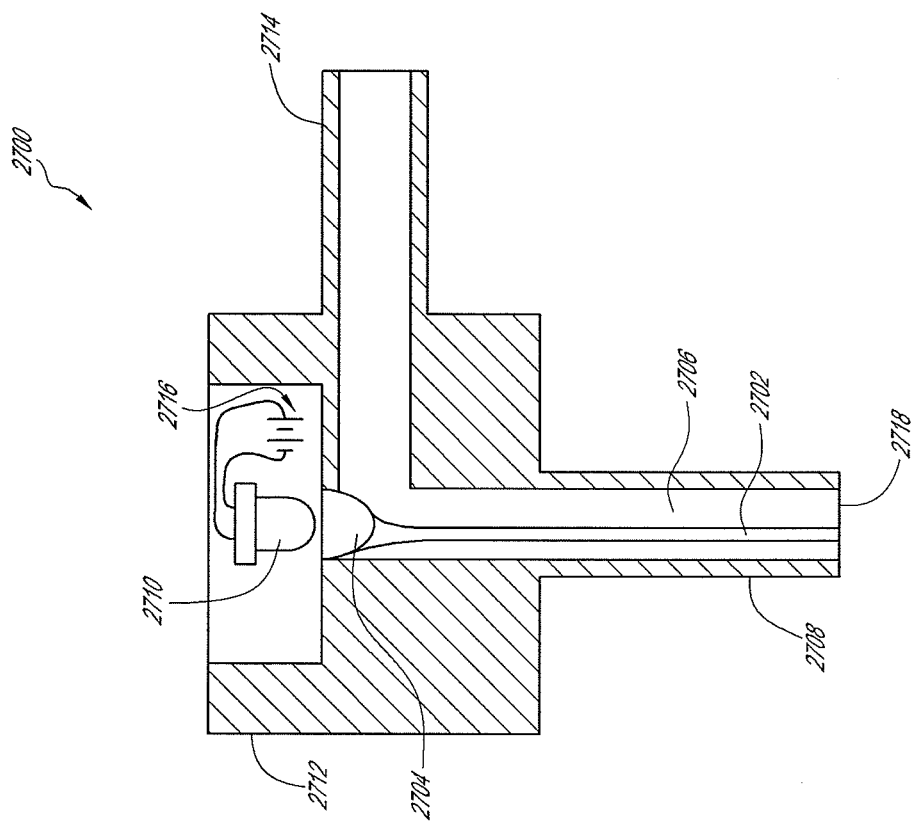
FIG. 27 is a side view of an embodiment of a self-contained illuminated infusion cannula system.

FIG. 27 is a cannula system 2700, similar to other embodiments described above, except that a length of fiber optic 2702 is coupled to a lens 2704. Fiber optic 2702, depending on the light illumination criteria, may extend partially or fully through lumen 2706 of cannula 2708. Because light source 2710 (preferably an LED, as shown) is contained in body 2712 adjacent lens 2704 more light may be transmitted to a surgical site compared to prior art embodiments having a remote light source transmitting light through a fiber optic length much longer than fiber optic 2702. The relatively short length of fiber optic 2702 (preferably less than 2 cm) causes less light loss compared to prior art fiber optic embodiments with fiber lengths of hundreds of centimeters. The lower light loss allows the use of a lower power consuming and lower light producing light source 2710 to produce an acceptable illumination level, compared to prior art embodiments.

Body 2712 also includes an infusion port 2714 for receiving fluid to be delivered to a surgical site through lumen 2706. Also, shown is a power source 2716 contained within the body 2712 for powering light source 2710. It is also possible with advances in LED technology that light source 2710 may be placed at distal end 2718 of cannula 2708 and still allow infusion fluid to flow to a surgical site through lumen 2706. If light source 2710 is placed at distal end 2718, an electrical connection may extend through lumen 2706, instead of fiber optic 2702, and connect to power source 2716 or to a remote power source connection (not shown).

Figure 28:
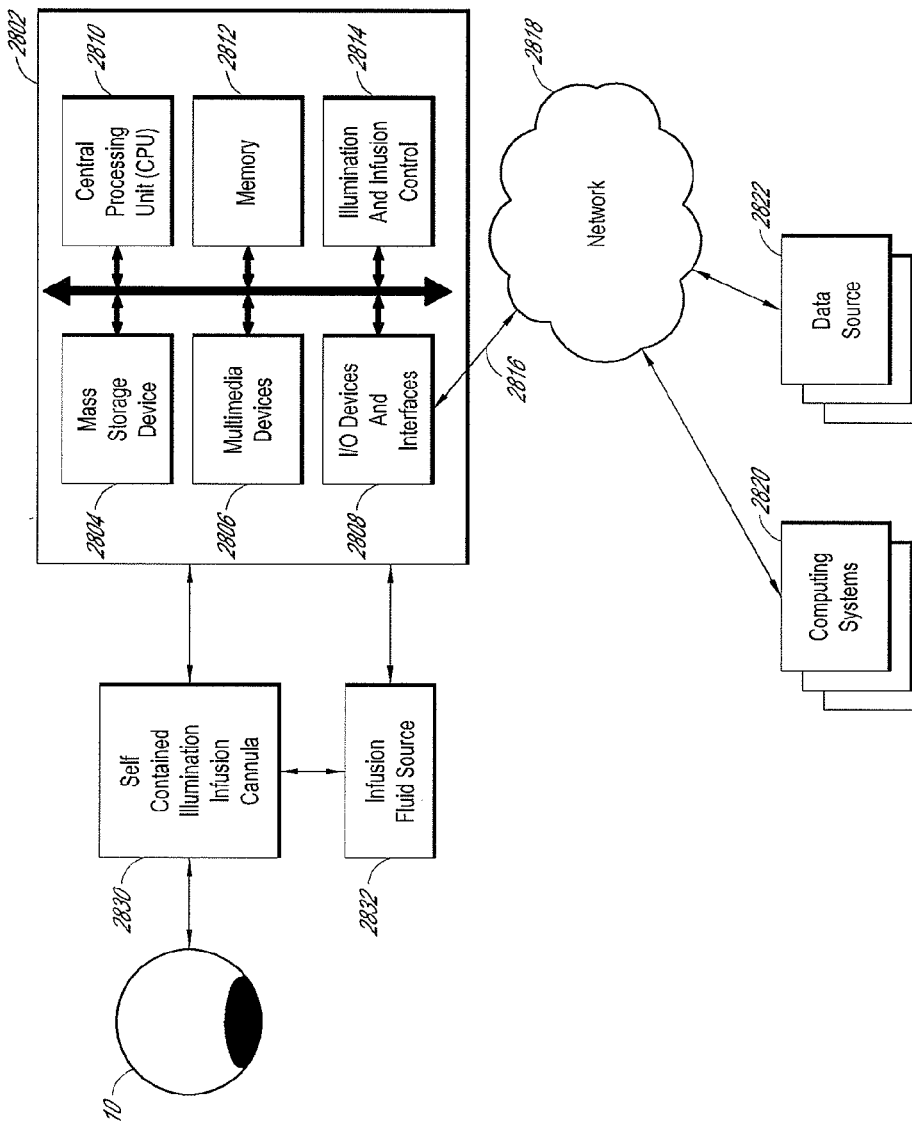
FIG. 28 shows a schematic view of an embodiment of a self-contained illuminated infusion cannula system and other components.

In some embodiments, the systems, processes, and methods described above are implemented using a computing system, such as the one shown in FIG. 28. The computer system 2802 is in communication with one or more computing systems 2820 and/or one or more data sources 2822 via one or more networks 2818, and in communication with a self-contained illumination infusion cannula 2830 and an infusion fluid source 2832. While FIG. 28 illustrates an embodiment of a computing system 2802, it is recognized that the functionality provided for in the components and modules of computer system 2802 may be combined into fewer components and modules, or further separated into additional components and modules.

Illumination and Infusion Control Module

The computer system 2802 includes an illumination and infusion control module 2814 that carries out the functions, methods, acts, and/or processes described herein. The illumination and infusion control module 2814 is executed on the computer system 2802 by a central processing unit 2810 discussed further below.

In general the word "module," as used herein, refers to logic embodied in hardware or firmware or to a collection of software instructions, having entry and exit points. Modules are written in a program language, such as JAVA, C or C++, or the like. Software modules may be compiled or linked into an executable program, installed in a dynamic link library, or may be written in an interpreted language such as BASIC letters, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems, and may be stored on or within any suitable computer readable medium, or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

Computing System Components

The computer system 2802 includes one or more processing units (CPU) 2810, which may include a microprocessor. The computer system 2802 further includes a memory 2812, such as random access memory (RAM) for temporary storage of information, a read only memory (ROM) for permanent storage of information, and a mass storage device 2804, such as a hard drive, diskette, or optical media storage device. Alternatively, the mass storage device may be implemented in an array of servers. Typically, the components of the computer system 2802 are connected to the computer using a standards based bus system. The bus system can be implemented using various protocols, such as Peripheral Component Interconnect (PCI), Micro Channel, SCSI, Industrial Standard Architecture (ISA) and Extended ISA (EISA) architectures.

The computer system 2802 includes one or more input/output (I/O) devices and interfaces 2808, such as a keyboard, mouse, touch pad, and printer. The I/O devices and interfaces 2808 can include one or more display devices, such as a monitor, that allows the visual presentation of data to a user. More particularly, a display device provides for the presentation of GUIs as application software data, and multi-media presentations, for example. The I/O devices and interfaces 2808 can also provide a communications interface to various external devices. The computer system 2802 may include one or more multi-media devices 2806, such as speakers, video cards, graphics accelerators, and microphones, for example.

Computing System Device/Operating System

The computer system 2802 may run on a variety of computing devices, such as a server, a Windows server, and Structure Query Language server, a Unix Server, a personal computer, a laptop computer, and so forth. In other embodiments, the computer system 2802 may run on a mainframe computer suitable for controlling and/or communicating with large databases, performing high volume transaction processing, and generating reports from large databases. The computing system 2802 is generally controlled and coordinated by an operating system software, such as z/OS, Windows 95, Windows 98, Windows NT, Windows 2000, Windows XP, Windows Vista, Windows 7, Lenox, BSD, SunOS, Solaris, or other compatible operating systems, including proprietary operating systems. Operating systems control and schedule computer processes for execution, perform memory management, provide file system, networking, and I/O services, and provide a user interface, such as a graphical user interface (GUI), among other things.

Network

The computer system 2802 illustrated in FIG. 28 is coupled to a network 2818, such as a LAN, WAN, or the Internet via a communication link 2816 (wired, wireless, or a combination thereof). Network 2818 communicates with various computing devices and/or other electronic devices. Network 2818 is communicating with one or more computing systems 2820 and one or more data sources 2822. The illumination and infusion control module 2814 may access or may be accessed by computing systems 2820 and/or data sources 2822 through a web-enabled user access point. Connections may be a direct physical connection, a virtual connection, and other connection type. The web-enabled user access point may include a browser module that uses text, graphics, audio, video, and other media to present data and to allow interaction with data via the network 2818.

The browser module or other output module may be implemented as a combination of an all-points addressable display such as a cathode ray tube (CRT), a liquid crystal display (LCD), a plasma display, or other types and/or combinations of displays. The output module may be implemented to communicate with input devices 2808 and they also include software with the appropriate interfaces which allow a user to access data through the use of stylized screen elements, such as menus, windows, dialogue boxes, tool bars, and controls (e.g., radio buttons, check boxes, sliding scales, and so forth). Furthermore, the output module may communicate with a set of input and output devices to receive signals from the user.

Other Systems

The computing system 2802 may include one or more internal and/or external data sources (e.g., data sources 2822). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 2802 as shown in FIG. 28 accesses one or more attribute filters. The attribute filters may be stored in a database or data repository. The computer system 2802 may access the one or more attribute filters through a network 2818 or may directly access the database or data repository through I/O devices and interfaces 2808. The data repository storing the one or more attribute filters may reside within the computer system 2802.

The computer system 2802 also accesses one or more consumer verification databases. The consumer verification databases may be stored in a database or data repository. The computer system 2802 may access the one or more consumer verification databases through a network 2818 or may directly access the database or data repository through I/O devices and interfaces 2808. The data repository storing the one or more consumer verification databases may reside within the computer system 2802.

Additional Embodiments

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The embodiments discussed above have been discussed in detail in connection with specific designs. It is to be understood, however, that skilled artisans will be able to implement inventive features by employing structures that may differ from the specific structures described above. Applicants in no way intend for the scope of the inventive features discussed herein to be limited to the specific structure used in certain embodiments. For example, the illustrated cannula system can provide illumination to arthroscopic or endoscopic procedures.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure, for example, the arrangement and combination of LED light sources and optical elements can be any suitable arrangement sufficient to illuminate the vitreous cavity, or any other applicable body cavity. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A cannula system comprising:
a body;
a light source contained within the body;
an infusion port formed in the body for receiving fluids to be delivered to a surgical site; and
a cannula formed with the body and having a lumen for delivering the fluids received through the infusion port and for transmitting light from the light source, wherein the light source is movable relative to the body for allowing a trocar to be inserted through the cannula to create an incision through which the cannula is inserted.

2. The system of claim 1, further comprising a lens held within the body between the light source and the cannula.

3. The system of claim 2, further including at least one length of fiber optic coupled to the lens and extending at least partially through the cannula.

4. The system of claim 1, further including a power source contained within the body for powering the light source.

5. The system of claim 1, further including a power source connected to and remote from the light source.

6. The system of claim 1, further including a light source-containing portion that is removable relative to the body.

7. The system of claim 1, the body comprising a cap, wherein the light source is contained in the cap.

8. The system of claim 1, wherein the cannula is transparent.

9. The system of claim 1, wherein the light source comprises at least one of a light emitting diode (LED), an organic light emitting diode (OLED), a light bulb, and a lamp.

10. A cannula system comprising:
a housing element having a lumen and a port configured to provide a flow of fluid to the lumen;
a light emitting diode light source positionable within the housing element, the light emitting diode light source configured to direct light through the lumen when disposed within the housing element; and
a trocar, the lumen sized to allow the trocar to pass through the lumen;
wherein a cannula defining the lumen is transparent and is configured to permit light to pass through the cannula defining the lumen from the light emitting diode light source to a surgical site, wherein the lumen is also configured to direct fluid to the surgical site.

11. The cannula system of claim 10, wherein the transparent cannula defining the lumen has a length capable of extending from an outer surface of an eye into an interior of the eye, the length being less than one-half of a diameter of the eye.

12. The cannula system of claim 10, further comprising a lens to direct light through the cannula defining the lumen.

13. The cannula system of claim 12, wherein the lens comprises a plurality of circumferential optical prism elements spaced along a length of the cannula defining the lumen.

14. The cannula system of claim 10, further comprising a power source for the light emitting diode light source.

15. The cannula system of claim 14, wherein the power source comprises at least one battery within the housing element.

16. The cannula system of claim 10, further comprising a phosphorescence material applied to the cannula defining the lumen, wherein light is dispersed from the lumen through the phosphorescence material.

* * * * *